(12) United States Patent
Kannar et al.

(10) Patent No.: US 11,730,178 B2
(45) Date of Patent: Aug. 22, 2023

(54) EXTRACTION METHOD

(71) Applicant: THE PRODUCT MAKERS (AUSTRALIA) PTY LTD, Keysborough (AU)

(72) Inventors: David Kannar, Victoria (AU); Barry James Kitchen, Victoria (AU); Lance Sparrow, Victoria (AU)

(73) Assignee: POLY GAIN PTE LTD, Focus One (SG)

( * ) Notice: Subject to any disclaimer, the term of this patent is extended or adjusted under 35 U.S.C. 154(b) by 40 days.

(21) Appl. No.: 17/502,784

(22) Filed: Oct. 15, 2021

(65) Prior Publication Data

US 2022/0279820 A1 Sep. 8, 2022

Related U.S. Application Data

(63) Continuation of application No. 16/197,733, filed on Nov. 21, 2018, now abandoned, which is a continuation of application No. 14/423,995, filed as application No. PCT/AU2013/000964 on Aug. 28, 2013, now abandoned.

(30) Foreign Application Priority Data

Aug. 28, 2012 (AU) ................................ 2012903726

(51) Int. Cl.
| | | |
|---|---|---|
| A61K 36/00 | (2006.01) | |
| A23L 2/60 | (2006.01) | |
| A23L 29/30 | (2016.01) | |
| A23L 27/30 | (2016.01) | |
| A23L 33/10 | (2016.01) | |
| C13B 10/06 | (2011.01) | |
| C13B 10/14 | (2011.01) | |
| A61K 36/899 | (2006.01) | |
| B01D 15/08 | (2006.01) | |
| A23L 33/125 | (2016.01) | |
| A23L 7/00 | (2016.01) | |
| A23L 21/00 | (2016.01) | |

(52) U.S. Cl.
CPC ............ *A23L 2/60* (2013.01); *A23L 27/33* (2016.08); *A23L 29/30* (2016.08); *A23L 33/10* (2016.08); *A61K 36/899* (2013.01); *B01D 15/08* (2013.01); *C13B 10/06* (2013.01); *C13B 10/14* (2013.01); *A23L 7/00* (2016.08); *A23L 21/00* (2016.08); *A23L 33/125* (2016.08)

(58) Field of Classification Search
None
See application file for complete search history.

(56) References Cited

U.S. PATENT DOCUMENTS

| | | |
|---|---|---|
| 1,730,473 A | 10/1929 | Olivarius et al. |
| 2,000,202 A | 5/1935 | Vasquez et al. |
| 2,170,713 A | 8/1939 | Fattinger et al. |
| 2,342,162 A | 2/1944 | Musher et al. |
| 3,174,877 A | 3/1965 | Bohrer et al. |
| 3,325,308 A | 6/1967 | Othmer et al. |
| 3,619,293 A | 11/1971 | Niimi et al. |
| 3,975,205 A | 8/1976 | Munir et al. |
| 4,101,338 A | 7/1978 | Rapaport et al. |
| 4,102,646 A | 7/1978 | Sleeter et al. |
| 4,111,714 A | 9/1978 | Hippchen et al. |
| 4,116,712 A | 9/1978 | Othmer et al. |
| 4,333,770 A | 6/1982 | Neuzil et al. |
| 4,359,430 A | 11/1982 | Heikkila et al. |
| 4,404,037 A | 9/1983 | Broughton et al. |
| 4,523,959 A | 6/1985 | Exertier et al. |
| 4,523,999 A | 6/1985 | Toyoshi et al. |
| 5,002,614 A | 3/1991 | Miyagi et al. |
| 5,096,594 A | 3/1992 | Rabinowitz et al. |
| 5,127,957 A | 7/1992 | Heikkila et al. |
| 5,252,136 A | 10/1993 | Desforges et al. |

(Continued)

FOREIGN PATENT DOCUMENTS

| | | |
|---|---|---|
| AU | 2011204847 A1 | 8/2011 |
| CA | 2053412 A1 | 4/1992 |

(Continued)

OTHER PUBLICATIONS

Actis-Goretta et al., Inhibition of Angiotensin Converting Enzyme Activity by Flavanol-Rich Foods; Journal of Agricultural and Food Chemistry, Jan. 2006, pp. 229-234, vol. 54, American Chemical Society.

(Continued)

*Primary Examiner* — Russell G Fiebig
(74) *Attorney, Agent, or Firm* — Brian C. Trinque; Lathrop GPM LLP

(57) ABSTRACT

The present invention relates to a process for producing an extract derived from sugar cane, the process comprising:
i) mixing a sugar cane derived product with ethanol to produce an extraction mixture comprising at least about 50% v/v ethanol;
ii) allowing a precipitate to form in the extraction mixture;
iii) removing the precipitate from the extraction mixture to obtain a supernatant; and
iv) removing ethanol from the supernatant to produce the extract derived from sugar cane.

The present invention further relates to extracts produced according to the process of the invention. The invention also relates to the use of such extracts in a method of lowering the available calorific value of a food or beverage, in treating or preventing disease, and as a nutritional supplement, dietary supplement, sports nutrition product, food coating or pharmaceutical product.

4 Claims, 13 Drawing Sheets

(56) References Cited

U.S. PATENT DOCUMENTS

| | | |
|---|---|---|
| 5,382,294 A | 1/1995 | Rimedio et al. |
| 5,384,035 A | 1/1995 | Smolnik et al. |
| 5,454,875 A | 10/1995 | Clarke et al. |
| 5,482,631 A | 1/1996 | Sasha et al. |
| 5,556,546 A | 9/1996 | Tanimura et al. |
| 5,578,336 A | 11/1996 | Monte |
| 5,663,156 A | 9/1997 | Granja et al. |
| 5,955,269 A | 9/1999 | Ghai et al. |
| 6,093,326 A | 7/2000 | Heikkila et al. |
| 6,099,654 A | 8/2000 | Kaneko et al. |
| 6,217,664 B1 | 4/2001 | Baniel |
| 6,372,049 B1 | 4/2002 | Shimanskaya et al. |
| 6,406,547 B1 | 6/2002 | Donovan et al. |
| 6,406,548 B1 | 6/2002 | Donovan et al. |
| 6,475,390 B1 | 11/2002 | Durham et al. |
| 6,528,099 B1 | 3/2003 | Garti et al. |
| 6,630,672 B1 | 10/2003 | Brotherton et al. |
| 6,723,369 B2 | 4/2004 | Burgess et al. |
| 6,777,397 B2 | 8/2004 | Zehner et al. |
| 6,869,625 B2 | 3/2005 | Gupta et al. |
| 6,885,003 B1 | 4/2005 | Dubernet et al. |
| 7,015,339 B2 | 3/2006 | Khare et al. |
| 7,150,885 B2 | 12/2006 | Araki et al. |
| 7,312,199 B2 | 12/2007 | Burdick et al. |
| 8,138,162 B2 | 3/2012 | Kannar et al. |
| 9,364,016 B2 | 6/2016 | Kannar et al. |
| 2001/0001178 A1 | 5/2001 | Donovan et al. |
| 2001/0001956 A1 | 5/2001 | Hyoky et al. |
| 2002/0150652 A1 | 10/2002 | Antila et al. |
| 2002/0169311 A1 | 11/2002 | Paanamen et al. |
| 2002/0187219 A1 | 12/2002 | Yang et al. |
| 2002/0197380 A1 | 12/2002 | Mantius et al. |
| 2003/0082287 A1 | 5/2003 | Wolt et al. |
| 2003/0124170 A1 | 7/2003 | Gallaher et al. |
| 2003/0124208 A1 | 7/2003 | Makino et al. |
| 2003/0147978 A1 | 8/2003 | Araki et al. |
| 2003/0161903 A1 | 8/2003 | Konishi et al. |
| 2003/0165574 A1 | 9/2003 | Ward et al. |
| 2003/0198694 A1 | 10/2003 | Chou et al. |
| 2003/0232763 A1 | 12/2003 | Jia et al. |
| 2004/0001862 A1 | 1/2004 | Xin et al. |
| 2004/0006222 A1 | 1/2004 | Paananen et al. |
| 2004/0006223 A1 | 1/2004 | Karki et al. |
| 2004/0052915 A1 | 3/2004 | Carlson et al. |
| 2004/0060868 A1 | 4/2004 | Heikkila et al. |
| 2004/0081734 A1 | 4/2004 | Lang et al. |
| 2004/0097429 A1 | 5/2004 | Nieuwenhuizen et al. |
| 2004/0131749 A1 | 7/2004 | Grabiel et al. |
| 2004/0151815 A1 | 8/2004 | Jensen et al. |
| 2004/0191336 A1 | 9/2004 | Hilaly et al. |
| 2004/0197380 A1 | 10/2004 | Wolf et al. |
| 2005/0175674 A1 | 8/2005 | Lang et al. |
| 2005/0181074 A1 | 8/2005 | Watson et al. |
| 2005/0214419 A1 | 9/2005 | Aberle et al. |
| 2006/0003029 A1 | 1/2006 | Nash et al. |
| 2006/0121158 A1 | 6/2006 | Ferruzzi et al. |
| 2006/0147556 A1 | 7/2006 | Brewer et al. |
| 2007/0014912 A1 | 1/2007 | Mazza et al. |
| 2007/0158269 A1 | 7/2007 | Paananen et al. |
| 2007/0160698 A1 | 7/2007 | Waga et al. |
| 2007/0166246 A1 | 7/2007 | Takagaki et al. |
| 2007/0178175 A1 | 8/2007 | Matsubara et al. |
| 2007/0190209 A1 | 8/2007 | Sinnott et al. |
| 2008/0286254 A1 | 11/2008 | Sakamoto et al. |
| 2009/0047368 A1 | 2/2009 | Numata et al. |
| 2009/0053333 A1 | 2/2009 | Sambanthamurthi et al. |
| 2009/0281057 A1 | 11/2009 | Bhaskaran et al. |
| 2010/0112099 A1 | 5/2010 | Tripp et al. |
| 2010/0130422 A1 | 5/2010 | Bernaert et al. |
| 2010/0166851 A1 | 7/2010 | Dallas et al. |
| 2010/0184666 A1 | 7/2010 | Bernaert et al. |
| 2010/0196549 A1 | 8/2010 | Rivera et al. |
| 2012/0115941 A1 | 5/2012 | Payn et al. |
| 2014/0315993 A1 | 10/2014 | Kannar et al. |

FOREIGN PATENT DOCUMENTS

| | | |
|---|---|---|
| CA | 2420881 A1 | 3/2002 |
| CN | 1484974 A | 3/2004 |
| CN | 1685929 A | 10/2005 |
| CN | 101317850 A | 12/2008 |
| DE | 3232693 A1 | 7/1983 |
| EP | 1362517 A1 | 11/2003 |
| EP | 1362919 A1 | 11/2003 |
| EP | 1447013 A1 | 8/2004 |
| EP | 1447014 A1 | 8/2004 |
| EP | 1466609 A1 | 10/2004 |
| FR | 2797688 A1 | 2/2001 |
| FR | 2929852 A1 | 10/2009 |
| JP | S-5359044 A | 5/1978 |
| JP | S-58144382 A | 8/1983 |
| JP | S 59-20223 A | 2/1984 |
| JP | S 61-69727 A | 4/1986 |
| JP | S 61-83130 A | 4/1986 |
| JP | S 61-139400 A | 6/1986 |
| JP | S 61-265068 A | 11/1986 |
| JP | S 61-268200 A | 11/1986 |
| JP | S 62-126951 A | 6/1987 |
| JP | S 63-207400 A | 8/1988 |
| JP | H-01244000 A | 9/1989 |
| JP | H-0220300 A | 1/1990 |
| JP | H-03145424 A | 6/1991 |
| JP | H-04320691 A | 11/1992 |
| JP | H-05211900 A | 8/1993 |
| JP | H-0662798 A | 3/1994 |
| JP | H-0840912 A | 2/1996 |
| JP | H-0925290 A | 1/1997 |
| JP | H-1175758 A | 3/1999 |
| JP | H 11318405 A | 11/1999 |
| JP | 2000-032954 A | 2/2000 |
| JP | 2000-297045 A | 10/2000 |
| JP | 2001-112439 A | 4/2001 |
| JP | 2001-131080 A | 5/2001 |
| JP | 2001-200250 A | 7/2001 |
| JP | 2001-302533 A | 10/2001 |
| JP | 2002-020306 A | 1/2002 |
| JP | 2002-161046 A | 6/2002 |
| JP | 2003-063975 A | 3/2003 |
| JP | 2003-116486 A | 4/2003 |
| JP | 2003-137803 A | 5/2003 |
| JP | 2004-065018 A | 3/2004 |
| JP | 2004-075612 A | 3/2004 |
| JP | 2004-331512 A | 11/2004 |
| JP | 2005-278407 A | 10/2005 |
| JP | 2005-343843 A | 12/2005 |
| JP | 2006-028020 A | 2/2006 |
| JP | 2006-131578 A | 5/2006 |
| JP | 2006-321772 A | 11/2006 |
| JP | 2007-043940 A | 2/2007 |
| JP | 2007-063221 A | 3/2007 |
| JP | 2008-044872 A | 2/2008 |
| JP | 2008-222656 A | 9/2008 |
| JP | 2009-298769 A | 12/2009 |
| KR | 100894911 B1 | 4/2009 |
| KR | 10-20090063794 A | 6/2009 |
| RU | 2048847 C1 | 11/1995 |
| WO | WO 1989/01295 A1 | 2/1989 |
| WO | WO 1994/12057 A1 | 6/1994 |
| WO | WO 1997/049734 A1 | 12/1997 |
| WO | WO 1998/29571 A1 | 7/1998 |
| WO | WO 1998/55658 A2 | 12/1998 |
| WO | WO 2001/036690 A1 | 5/2001 |
| WO | WO 2001/078629 A1 | 10/2001 |
| WO | WO 2002/014477 A2 | 2/2002 |
| WO | WO 2002/020112 A1 | 3/2002 |
| WO | WO 2002/078469 A1 | 10/2002 |
| WO | WO 2003/074144 A2 | 9/2003 |
| WO | WO 2003/074145 A1 | 9/2003 |
| WO | WO 2003/075685 A2 | 9/2003 |
| WO | WO 2003/099309 A1 | 12/2003 |
| WO | WO 2004/014159 A1 | 2/2004 |
| WO | WO 2005/006891 A1 | 1/2005 |
| WO | WO 2005/052195 A1 | 6/2005 |
| WO | WO 2005/084457 A1 | 9/2005 |

(56) References Cited

FOREIGN PATENT DOCUMENTS

| | | |
|---|---|---|
| WO | WO 2005/089066 A2 | 9/2005 |
| WO | WO 2005/105852 A1 | 11/2005 |
| WO | WO 2005/117608 A1 | 12/2005 |
| WO | WO 2006/014028 A1 | 2/2006 |
| WO | WO 2006/052007 A1 | 5/2006 |
| WO | WO 2006/128253 A1 | 12/2006 |
| WO | WO 2006/128259 A1 | 12/2006 |
| WO | WO 2007/041817 A1 | 4/2007 |
| WO | WO 2008/034180 A1 | 3/2008 |
| WO | WO 2008/142178 A1 | 11/2008 |
| WO | WO 2009/046492 A1 | 4/2009 |
| WO | WO 2009/049428 A1 | 4/2009 |
| WO | WO 2009/136219 A1 | 11/2009 |
| WO | WO 2010/094837 A2 | 8/2010 |
| WO | WO 2010/094860 A2 | 8/2010 |
| WO | WO 2010/118474 A1 | 10/2010 |
| WO | WO 2012/106761 A1 | 8/2012 |

OTHER PUBLICATIONS

Anderson, 2008, Proc. Nutrition Soc., 67:48-53.
Altukhov et al., 2004, Human Physiol, 30(2):216-223.
Baba et al. 2005 Eur. J. Nutr., 44:1-9.
Badescu et al. 2005, Rom. J. Physiol. 42:1-4, pp. 103-120.
Bahadoran et al., Journal of Diabetes & Metabolic Disorders, 12:43, 9 pages, 2013.
Balasubramanian et al., 2010, Carcinogenesis 31(3):496-503.
Banini et al., 2006, Nutrition 22:1137-1145.
Barclay et al., The Australian Paradox: A Substantial Decline in Sugars Intake over the Same Timeframe that Overweight and Obesity Have Increased; Nutrients, Apr. 20, 2011, vol. 3, MDPI AG.
Basu et al., 2010, J. Nutr., 140:1582-1587.
Bento et al., 1997, SIT Poster #722 Publ. Techn. Papers Proc. Ann. Met Sugar industry Technologists 56:383-392, "Gel Permeation Chromatography of Sugar Material Using . . . ".
Bento et al., 1997, Intl. Sugar J., 99 (1187 Suppl.):555-562.
Bento et al., 1998, Carbohydrate Polymers 37:257-261.
Berhow et al., 2000, Mutation Res., 448:11-22.
Bray et al., "Current and Potential Drugs for Treatment of Obesity," 1999, Endocrine Rev20(6):805-875.
Brown et al., 2009, Br. J. Nutr., 101:886-894.
Bureau of Sugar Experiment Stations (BSES), "Laboratory Manual for Australian Sugar Mills," Apr. 2001, 2 pages; vol. 2, Method 33, BSES Brisbane.
Burkon et al., 2008, Mol. Nutr. Food Res., 52:549-557.
Cai et al., The Rice bran constuent tricin potently inhibits cycloxygenase enzymes and interferes with intestinal carcinogenesis in ApcMin mice, Molecular Cancer Therapeutics, Sep. 2005, pp. 1287-1292, vol. 4, No. 9, American Association of Cancer Research.
Chajuss, 2004, "Soy Molasses: Processing and Utilization as a Functional Food," In: Soybeans as Functional Foods and ingredients, Liu et al., Eds.
Clarke et al., "Polyfructose: A New Microbiol Polyssacharide," In: Carbohydrates as Organic Raw Materials, Lichtenthaler, Ed., VCH. Weinheim, 1990.
Coca et al., 2005, Chemosphere 60:1408-1415.
Colombo et al., Determination of flavonoids in cultivated sugarcane leaves, bagasse, juice and in transgenic sugarcane by liquid chromatography-UV detection, Journal of Chromatography A, Nov. 2005, pp. 118-124, vol. 1103, Elsevier B.V.
Colombo et al., On-line identification of further flavone C-and O-Glycosides from Sugarcane (*Saccharum officinarum* L., Gramineae) by HPLA-UV-MS; Phytochemical Analysis, Jul. 2006, pp. 337-343, vol. 17, John Wiley & Sons, Ltd.
Dallas et al., 2008, Phytomedicine 15:783-792.
Dal-Pan et al., 2010, BMC Physiol., 10:11.
Deseo et al., Food Chemistry, 314:126180, 10 pages, 2020.
Ding et al., Journal of Nutritional Biochemistry, 21:941-947, 2020.
Dong et al., "A Functional Oliogsaccharide in Sugar Beet—Raffinose," China Beet & Sugar, No. 3, Sep. 2001, pp. 24-26.

Duarte-Almeida et al., Antioxidant Activity of Phenolics Compounds From Sugar Cane (*Saccharum officinarum*) Juice, Plant Foods for Human Nutrition, Dec. 2006, pp. 187-192, vol. 61, Springer Science+Business Media, Inc.
Edye et al., 1998, "The Fate of Soluble Sugarcane Polysaccharides in Sugar Manufacture," Poster.
Fahey et al. (1976) "Influence of molasses lignin-hemicellulose fractions in rat nutrition," The Journal of Nutrition. 106(10):1447-1451.
Fernandes et al., 2009, Talanta 79:222-228.
Frank et al., 2009, J. Nutr. 139:58-62.
Fujita et al., 2000, Abstract AGFD-086, Book of Abstracts, 219th ACS National Meeting, San Francisco, CA, Amer. Chem. Soc., Washington, DC.
Fukino et al., 2005, J. Nutr. Sci., Vitaminol., 51:335-342.
Fukino et al., 2008, Eur. J. Clin. Nutr., 62:953-960.
"Gekkan Food Chemical," 2001, pp. 72-81, vol. 17, No. 10 (English translation of abstract only).
Godshall, High Molecular Weight Colourants; Sucropedia.com, Sep. 29, 2009, 4 pages, www.sucropedia.com.
Goossens, G.H. et al., "Possible Involvement of the Adipose Tissue Renin-Angiotensin System in the Pathophysiology of Obesity and Obesity-Related Disorders," 2003, Obesity Rev., 4:43-55.
Han et al. "Anti-Obesity Action of Salix matsudana Leaves (Part 1) Anti-Obesity Action by Polyphenols of Salix Matsudana in High Fat-Diet Treated Rodent Animals," 2003, Phytotherapy Res., 17:1188-1194.
Hangyal, 1969, Cukoripar22(5):183-186 (Abstract Only; HCAPLUS database record No. 1970:123241).
Hatano et al., 2008, Chemosphere 71:1730-1737.
Hollis et al., 2009, J. Amer. Coll. Nutr., 28(5):574-582.
Hu et al., 2006, Zhongguo Linchuang Kangfu 10(43):79-81 (Abstract Only).
Ishikura et al., 2008, Jap. Pharmacol Therapeut., 36(10):931-939.
Islam, 2008, Z. Naturforsch 63c:233-240.
Jacome et al., 2009, Alim. Nutr., 20(2):185-190.
Ji et al., J. Am. Coll. Nutr., https://doi.org/10.1080/07315724.2019.1587323, 2019.
Kajimoto et al., "Tea Catechins with a Galloyl Moiety Reduce Body Weight and Fat," 2005, J. Health Sci., 51(2):161-171.
Kantachote, 2009, "Microbial succession in a fermenting of wild forest noni (*Morinda coreia* Ham) fruit plus molasses in its role in producing a liquid fertilizer," Electr. J. Biotechnol. 12(3):12.
Khan et al., 2010, Journal of Experimental Biology, 61(15):4185-4196.
Kim et al., "Antioxidant capacity of phenolic phytochemicals from various cultivars of plums," Food Chemistry, 2003, pp. 321-326, 81.
Kim et al. Nutrients 8:17 (27 pages) 2016.
Kishihara et al., 1986, Kagaku Kogaku Ronbunshu 12(2): 199-205 (Abstract Only).
Kita et al., 2004, BioFactors 22:259-263.
Klasing et al. (1985) "Biological activity of phenolic compounds. Hepatic cytochrome P-450, cytochrome b5, and NADPH cytochrome c reductase in chicks and rats fed phenolic monomers, polymers, and glycosides," Proc. Soc. Exp. Biol. Med. 179:529-538.
Koge K. et al., Antioxidants and Other Functional Extracts from Sugarcane, Chapter 15, 411-431, (2005).
Kovacs et al., 2004, Br. J. Nutr., 91:431-437.
Kumar et al., "Effect of Long Term Feeding of Urea Molasses Liquid Diet (UMLD) on Ovarian Activity in Crossbred Heifers," 1998 Indian Vet. Med. J., 22:185-188.
Lee et al., 2008, Hanguk Sikpum Yongyang Kwahak Hoechi 37(5):561-570 (Abstract Only).
Lee et al. J. Agric. Food Chem. 66: 9989-9994, 2018.
Livesey et al., "Fructose Consumption and Consequences for glycation, plasma triacylglycerol, and body weight: meta-analyses and meta-regression models of intervention studies," The American Journal of Clinical Nutrition, Nov. 2008, pp. 1419-1437, vol. 88, American Society for Nutrition.
Loke et al., 2010, Arterioscler. Thromb. Vasc. Biol., 30:749-757.

(56) References Cited

OTHER PUBLICATIONS

Lo Piparo et al., Flavonoids for Controlling Starch Digestion: Structural Requirements for Inhibiting Human alpha-Amylase, Journal of Medicinal Chemistry, May 2008, pp. 3555-3561, vol. 51, No. 12, American Chemical Society.
Machowetz et al., 2008, Horm. Metab. Res., 40:697-701.
Mantovani et al., 2004, Cancer Epidemiol. Biomarkers Prev., 13(10):1651-1659.
Mantovani et al., 2006, Cancer Epidemiol. Biomarkers Prev. 15:1030-1034.
Mantovani et al., 2008, Nutrition 24:305-313.
Mehra et al., "Effect of Restricted and Ad libilum Feeding of Urea Molasses Liquid Diet (UMLD) on the Performance of Adult Crossbred Cattle," 1998, Asian-Asutralasian J Animal Sci:11(1):30-34.
Melby et al., 2007, Daizu Tanpakushitsu Kenkyu 9:138-146 (Abstract Only).
Nagao et al., 2009, Jap. Pharmacol. Therapeut., 37(4):333-344 (Abstract Only).
Nagasako-Akazome et al., 2007, J. Oleo. Sci., 56(8):417-428.
Nakamura et al., 2007, Jap. Pharmacol. Therapeut. 35(6):661-671.
Nakamura et al., 2008, Jap. Pharmacol. Therapeut. 36(4):347-357 (Abstract Only).
Ochiai et al., 2009, Hypertensions Res., 32:969-974.
Olthof et al., 2000, "Metabolism of Chlorogenic Acid, Querctein-3-rutinoside and . . . " In: Spec. Publ. Royal Soc. Chem: 255 Dietary Anticarcinogens and Antimutagens, pp. 73-75.
Onimawo et al., 2010, African J. Food Agric. Nutr. Develop. 10(5): May 2010, pp. 2570-2586, ISSN 1684 5374.
Palfi et al., 2009, J. Nutr. Biochem. 20:418-425.
Pasman et al., "Effect of two breakfasts, different in carbohydrate composition on hunger and satiety and mood in healthy men," International Journal of Obesity 27:663-668, (2003).
Patton et al., "Use of a spectrophotometric bioassay for determination of microbial sensitivity to Manuka honey," Journal of Microbiological Methods, 2006, pp. 84-95, vol. 64.
Payet et al., Assessment of Antioxidant Activity of Cane Brown Sugars by ABTS and DPPH Radical Scavenging Assays Determination of Their Polyphenolic and Volatile Constituents, Journal of Agricultural and Food Chemistry, Dec. 2005, pp. 10074-10079., vol. 53, American Chemical Society.
Payet et al., "Comparison of the Concentrations of Phenolic Constituents in Cane Sugar Manufacturing Products with their Antioxidant Activities," J. Agric. Food Chem., 2006, pp. 7270-7276, vol. 54.
Pena et al., 2003, Chemosphere 51:893-900.
Qu et al., 2007, j. Clin. Rehabil. Tiss. Eng. Res., 11(43):8805-8808.
Robertson, "The Selective Removal of Final Molasses Components by Ethanolic Precipitation," Proceedings of the South African Sugar Technologists' Association, Jun. 1978, pp. 85-88.
Rosenberg et al., 1956, "Response of Growing and Mature Pullets to Continuous Feeding of Cane Final Molasses," Hawaii Agricultural Experiment Station Technical Paper No. 349.
Schoen et al., 2009, Nutrition 25:499-505.
"Shokuhin to Kaihatus," 2000, pp. 15-18, vol. 35, No. 6 (English translation of abstract only).
Shore et al., 1984, Sugar Technol. Rev., 12:1-99.
Sies et al., 2005, J. Nutrition 135(5):969-972.
Silventoinen et al., Trends in obesity and energy supply in the Who Monica Project, International Journal of Obesity, May 2004, pp. 710-718, vol. 28, Nature Publishing Group.
Simonetti et al., 2001, Meth. Enzymol. 335:122-130.
Singleton et al., "Colorimetry of total phenolics with phosphomolybdic-phosphotungstic acid reagents," Am. J. Enol. Vitic, 1965, pp. 144-158, 16.
Staunton et al., "Development of an online bagasse analysis system using NIR spectrsocopy," International Sugar Journal, 2007, pp. 482-488, 109.
Staunton et al., "On-line can analysis by near infra-red spectroscopy," Proc. Aust. Soc. SugarCane Technol., 1999, pp. 20-27, 21.
Stracke et al., 2010, Eur. J. Nutr. 49:301-310.
Tominaga et al., 2006, J. Health Sci., 52(6):672-683.
Vercellotti et al., 1996, Proc. Conf. Sugar Processing Res., SPRI, New Orleans, 321-349.
Vercellotti et al., 1998, "Mebrane Separation Chemistry in Sugar Processing Applications, Proceedings of the Conference on Sugar Processing Research," Savannah, GA, pp. 248-282.
Vercellotti et al., 1998, SIT Paper 727, Sugar Industry Technologists Annual Meeting, Marseille France, pp. 49-78.
Vermunt et al., Effects of sugar intake on body weight: a review, Obesity Reviews, May 2003, pp. 91-99, vol. 4, The International Association for the Study of Obesity.
Wachowicz, 1978, Gazeta Cukrownicza 86:125-127 (Abstract Only: HCAPLUS database record No. 1978:548469).
Wang et al., 2008, Carbohydrate Polymers 74:127-132.
Weisinger et al., Sugarcane-derived polyphenols decrease diet-induced obesity (Abstract), Appetite, Jun. 2009, p. 864, vol. 52, Elsevier.
Winter et al., 1992, J. Exp. Mar. Biol. Ecol., 155:263-277.
Wu et al., 2002, Huanjing Wuran Yu Fangzhi 24(1):13-18 (Abstract Only; HCAPLUS database record No. 2002:439963).
Wu et al., 2005, Carcinogenesis 26(5):976-980.
Yessenkyzy et al. Nutrients 12:1344 (32 pages), 2020.
Yinfa Zhang et al., "Application of Food Glycemic Index in Diabetes Nutrition Education," Acta Nutrimenta Sinica, Sep. 2003, vol. 25, No. 3, pp. 248-251.
Yoshikawa M. et al., "Medicinal Foodstuffs. III. Sugar Beet (1): Hypoglycemic Oleanolic Acid Oligoglycosides, Betavulgarosides I, II, III, and IV, from the Root of *Beta vulgaris* L., (Chenopodiaceae)" Chemical and Pharmaceutical Bulletin, Pharmaceutical Society of Japan, Tokyo, JP; vol. 44, No. 6, Jan. 1, 1996, pp. 1212-1217.
Zemel, M. "Regulation of Adiposity and Obesity Risk by Dietary Calcium: Mechanisms and Implications," 2002, J. Am. Coll. Nutr., 21(2):1, 146S-151S.
Zhang et al., 2007, Can. J. Physiol. Pharmacol. 85:1116-1123.
Zhang et al., 2009, Zhongguo Difangbingxue Zazhi 28(4):381-385 (Abstract Only).
Zheng et al., "Anti-Obesity Effects of the Three Major Components of Green Tea, Catechins, Caffeine and Theanine in Mice," Anti 2004, In Vivo 18:55-62.
Zielinska-Przyjemska et al., 2005 Polski Merkuriusz Lekarski 19(109):41-47 (Abstract Only).
Zieuinska-Przyjemska et al.,2007 Acta Sci. Pol. Technol. Aliment. 6(3):75-87.

Spectrum at time 25.50 min.

Spectrum at time 32.90 min.

Spectrum at time 34.10 min.

Spectrum at time 41.00 min.

EXTRACTION METHOD

CROSS-REFERENCE TO RELATED APPLICATIONS

This application is a continuation of U.S. patent application Ser. No. 16/197,733, filed Nov. 21, 2018, which is a continuation of U.S. patent application Ser. No. 14/423,995, filed Feb. 25, 2015, which is a 35 U.S.C. § 371 filing of International Patent Application No. PCT/AU2013/000964, filed Aug. 28, 2013, which claims priority to Australian Patent Application No. 2012903726, filed Aug. 28, 2012. The entire contents of these applications are incorporated herein by reference in their entirety.

FIELD OF THE INVENTION

The present invention relates to extracts derived from sugar cane and the subsequent processing streams (e.g., raw sugar, molasses, bagasse, mill mud and field trash). The present invention also relates to processes for producing the extracts. The present invention further relates to use of the extracts to reduce the available calorific value and/or glycaemic index of foods and beverages, and to use of the extracts in methods of treating or preventing diseases such as diabetes and metabolic syndrome as well as underlying conditions including but not limited to inflammation.

BACKGROUND

After being mechanically harvested, sugar cane is transported to a primary mill and crushed between serrated rollers. The crushed sugar cane is then pressed to extract the raw sugar juice, while the bagasse (leftover fibrous material) is used for fuel. The raw juice is then heated to its boiling point to extract any impurities, then lime and bleaching agents are added and mill mud is removed. The raw juice is further heated under vacuum to concentrate and increase Brix value. The concentrated syrup is seeded to produce bulk sugar crystals and a thick syrup known as molasses. The two are separated by a centrifuge and the molasses waste stream is collected for use as a low-grade animal feedstock. The sugar refining process thus generates a large number of products including raw juice, bagasse, mill mud, clarified juice, molasses, dunder and sugar crystals. Dunder is produced when sugar or molasses is fermented under controlled conditions to produce ethanol.

The bulk sugar crystals from the above process are further refined to produce many commercially available sugar products. For example, the further refining may include mixing the bulk sugar crystals with a hot concentrated syrup to soften the outer coating on the crystals. The crystals are then recovered by centrifuge and subsequently dissolved in hot water, a step that is sometimes called affination. This sugar liquor is then further purified by carbonation or phosfloatation, filtration, decolourisation and then seeded with fine sugar crystals. Once the crystals have grown to the requisite size, the crystals are separated from the syrup by centrifugation, then dried, graded and packaged. There may be several repetitions of recovering sugar crystals from the sugar liquor. The dark sugar syrup which is left after all of the sugar crystals have been recovered is also called refinery molasses.

Molasses and other products of the sugar refining process, especially the thick syrups and juices, are complex mixtures of substances. Typically they are difficult to refine further and there are often substances in the compositions that poison standard separating materials. Molasses and the other thick syrups and juices typically comprise polyphenols, polysaccharides, flavonoids, peptides and proteins, minerals, organic acids, and mono and disaccharides. Complex polymers are also formed during processing (e.g., melanoidins).

The key consideration with a primary sugar milling operation is to maximise the extract and recovery of sucrose. Similarly, the key consideration for sugar refineries processing primary mill sugar is to improve sucrose purity. Ethanol has been used in the recovery of sucrose from waste streams such as molasses (U.S. Pat. No. 1,730,473) and removal of impurities (U.S. Pat. Nos. 4,116,712; 2,000,202). Ethanol has also been used in the isolation of individual polyphenols from dunder, including tricin, luteolin or apigenin (WO 2004/014159). In this prior art process, ethanol was first used in a crude clean up step to crash out impurities and then as part of a solvent mixture to chromatographically isolate fractions comprising specific polyphenols.

Molasses, golden syrup and treacle have been used as a health food since the early 20th century and there have been claims that they are good therapies or cures for a wide range of disorders. Recent evidence demonstrates that novel sugar cane phytochemicals contained in the products of the sugar cane refining process reduce glycaemic index (GI) and therefore reduce the risk of obesity and diabetes. However the strong taste of these sugar cane derived products containing high molecular weight colourants makes them unpalatable to many people and the high viscosity of treacle and molasses makes them difficult to handle and unstable for incorporation into other foodstuffs. The other products of cane sugar refining such as bagasse and mill mud are known to include potentially useful substances but their hitherto intractable nature and instability has meant that they are usually thrown away as waste.

Extracts derived from sugar cane containing isolated polyphenols have been produced previously but are not as effective as complex mixtures of polyphenols and flavonoids derived from sugar cane products. Extracts derived from sugar cane containing mixtures of polyphenols and flavonoids have been produced previously but are dark coloured and bitter tasting, thus reducing the palatability and/or appearance of the finished food or beverage to which they are added. Accordingly, it is desirable to develop an improved extraction method that results in a sugar cane derived extract having an increased concentration of polyphenols, lower colour and decreased bitterness to avoid the palatability problems associated with known extracts. Extracts with these improved properties would find broader use in foods, nutraceuticals and pharmaceuticals compared to current offerings.

SUMMARY OF THE INVENTION

The present inventors have developed a process for producing a sugar cane derived extract comprising polyphenols and/or flavonoids in more functionally effective amounts and having improved taste, lower colour and polysaccharide content. The extracts of the present invention are believed to provide a synergistic combination of polyphenols and other components that are not contemplated in the prior art. As a consequence, the extract can be added back to foods or beverages in smaller quantities without significantly affecting the palatability and/or colour of the product.

Accordingly, in one aspect the present invention provides a process for producing an extract derived from sugar cane, the process comprising:

i) mixing a sugar cane derived product with ethanol to produce an extraction mixture comprising at least about 50% v/v ethanol;
ii) allowing a precipitate to form in the extraction mixture;
iii) removing the precipitate from the extraction mixture to obtain a supernatant; and
iv) removing ethanol from the supernatant to produce the extract derived from sugar cane.

The extract may be a powder, including a freeze dried powder or dehydrated powder. Preferably, the extract is a liquid extract, more preferably an aqueous extract.

In one embodiment, the process may further include:
i) mixing the sugar cane derived product with ethanol to produce a preliminary extraction mixture (e.g., comprising at least about 25% v/v ethanol);
ii) allowing a precipitate to form in the preliminary extraction mixture; and
iii) removing the precipitate from the preliminary extraction mixture to obtain a preliminary supernatant.

The preliminary supernatant may then be subjected to the process of the invention described above.

As will be apparent to the skilled person, isopropanol can be used in place of ethanol. As will also be apparent to the skilled person, any suitable food grade polar solvents could also be used in place of ethanol. Suitable food grade polar solvents include butanol, acetone, ethyl acetate and/or propyl acetate.

In one embodiment, the process further comprises removing water from the extract, preferably by evaporation under vacuum, to produce an aqueous extract having about 65° Bx (Brix).

Any suitable waste product from the sugar cane milling or refining process may be used as the sugar cane derived product in the process of the invention. In one embodiment, the sugar cane derived product is selected from molasses, bagasse, first expressed juice, mill mud, clarified sugar juice, clarified syrup, treacle, golden syrup, field trash, cane strippings and/or dunder.

In one particular embodiment, the sugar cane derived product is molasses or dunder, preferably molasses.

The skilled person will appreciate that in some instances the sugar cane derived product is mixed with water in order to enable efficient and/or uniform mixing of the sugar cane product with ethanol to form the extraction mixture. Accordingly, in one embodiment, the sugar cane derived product comprises a mixture of water with a product selected from molasses, bagasse, first expressed juice, mill mud, clarified sugar juice, clarified syrup, treacle, golden syrup, field trash, cane strippings and/or dunder.

In instances where the sugar cane derived product comprises solid components, it may be desirable to first blend or homogenise the sugar cane derived product prior to mixing it with ethanol to form the extraction mixture. Thus, in another embodiment, the sugar cane derived product is bagasse, field trash and/or cane strippings blended or homogenised with water.

The skilled person can readily determine a suitable period of time for allowing the precipitate to form in the reaction mixture. In one embodiment, the precipitate is allowed to form for about 10 minutes to about 24 hours prior to removing the precipitate.

In one embodiment, the precipitate is removed from the extraction mixture by filtration, centrifugation, and/or by allowing the precipitate to settle.

In another embodiment, the extraction mixture is maintained at a temperature of about 20° C. to about 30° C.

In yet another embodiment, the ethanol is removed from the supernatant by evaporation under vacuum.

In one embodiment, the process is performed in batch. In an alternative embodiment, the process is performed in continuous flow.

In another embodiment, the process further comprises subjecting the supernatant to membrane filtration and/or ion exchange, hydrophobic or size exclusion chromatography and collecting one or more flavonoid and/or polyphenol containing fractions to produce the extract derived from sugar cane.

Preferably, the extract derived from sugar cane comprises a mixture of flavonoids and/or polyphenols. More preferably, the extract further includes components that exist with flavonoids and/or polyphenols in sugar cane including minerals, vitamins, carbohydrates, organic acids and/or fiber. More preferably, the extract comprises a mixture of flavonoids and/or polyphenols as glycones and aglycones.

In one embodiment, the supernatant is subject to size exclusion membrane filtration or size exclusion chromatography.

In another embodiment, the process further comprises subjecting the supernatant to ion exchange chromatography, hydrophobic interaction chromatography, liquid chromatography-mass spectrometry (LCMS) and/or matrix-assisted laser desorption/ionization-time of flight (MALDI-TOF) to produce the extract, preferably hydrophobic interaction chromatography.

In one embodiment, the process further comprises subjecting the supernatant to hydrophobic interaction chromatography on food grade resin, preferably FPX66 or similar grades.

In one embodiment of the process of the invention, the extraction mixture comprises about 70% to about 85% ethanol.

In one embodiment, the extract comprises one or more of tricin, apigenin, luteolin, caffeic acid, hydroxycinnamic acids, sinapic acid, and derivatives thereof.

In one embodiment, the extract produced by the process of the invention has reduced colour per unit concentration of polyphenols when compared to prior art compositions. The colour of the extract may be analysed by measuring the absorbance of the supernatant at 420 nm. Preferably, the supernatant has an absorbance at 420 nm of about 800 to about 140 milliabsorbance (mAU) units. The colour of the extract may also be analysed using the ICUMSA protocol.

In another aspect, the present invention provides an extract produced by the process of the invention.

In one embodiment, the extract produced by the process of the invention comprises at least 25 mg/ml flavonoids and/or at least 25 mg/ml polyphenols.

In one particular embodiment, the extract produced by the process of the invention comprises one or more of tricin, apigenin, luteolin, caffeic acid, hydroxycinnamic acids, sinapic acid, and derivatives thereof.

In one embodiment, the extract produced by the process of the invention has α-glucosidase inhibitory activity and/or α-amylase inhibitory activity.

In one embodiment, the extract produced by the process of the invention has anti-inflammatory activity.

In one embodiment, the extract produced by the process of the invention has calorific value reduction properties and/or activity which slows the flux of carbohydrates, particularly monosaccharides, from the gut into the blood. Optionally, the extract also has glycemix index reduction properties.

In yet another aspect, the present invention provides an extract derived from sugar cane, wherein the extract comprises at least 25 mg/ml flavanoids, and/or at least 25 mg/ml polyphenols.

In one embodiment, the extract derived from sugar cane comprises one or more of tricin, apigenin, luteolin, caffeic acid, hydroxycinnamic acids, sinapic acid, and derivatives thereof.

In another embodiment, the extract derived from sugar cane has α-glucosidase inhibitory activity and/or α-amylase inhibitory activity.

In one embodiment, the extract derived from sugar cane has anti-inflammatory activity.

In one embodiment, the extract derived from sugar cane has calorific value reduction properties and/or activity which slows the flux of carbohydrates, particularly monosaccharides, from the gut into the blood. Optionally, the extract also has glycemix index reduction properties.

In another aspect, the present invention provides a composition comprising the extract of the invention.

In one embodiment, the composition is a nutraceutical, dietary supplement, sports nutrition product, food coating or pharmaceutical composition. Preferably, the composition is a dietary supplement or a pharmaceutical composition.

In another embodiment, the composition may include one or more additional active ingredients. Active ingredients may include, but are not limited to, fucodian and arcabose. It is believed that such combinations may have a synergistic effect.

In another aspect, the present invention provides a food or beverage comprising the extract of the invention or the composition of the invention.

In one embodiment, the food or beverage is selected from a bakery product, crystallised sugar, confectionary, breakfast cereal, naturally derived fiber, chemically derived fiber, dairy product, soft drink, water, coffee, cocoa, tea, or alcoholic beverage.

In another embodiment, the food or beverage is a soft drink selected from a fruit juice containing beverage and a carbonated soft drink.

In another aspect, the present invention provides a method of lowering the glycaemic index of a food or beverage, the method comprising adding the extract of the invention, and/or the composition of the invention, to the food or beverage.

In another aspect, the present invention provides a method of reducing the available calorific value of a food or beverage, the method comprising adding the extract of the invention, and/or the composition of the invention, to the food or beverage. In addition, or alternatively, the method comprises administering the composition of the invention to a subject prior to, in conjunction with, or after consumption of the food or beverage.

In one embodiment, the food or beverage is selected from a bakery product, crystallised sugar, confectionary, breakfast cereal, naturally derived fiber, chemically derived fiber, diary product, soft drink, water, coffee, cocoa, tea, or alcoholic beverage.

In one particular embodiment, the food is crystallised sugar.

In another aspect, the present invention provides a method of treating or preventing disease in a subject, the method comprising administering to the subject the extract of the invention, the composition of the invention, and/or the food or beverage of the invention.

In one embodiment, the disease that is treated or prevented is diabetes and/or metabolic syndrome. In one particular embodiment, the diabetes is type II diabetes. In another embodiment, the diabetes is type I diabetes.

In another aspect, the present invention provides the extract of the invention, the composition of the invention, and/or the food or beverage of the invention, for use in the treatment or prevention of disease.

In another aspect, the present invention provides use of the extract of the invention, the composition of the invention, and/or the food or beverage of the invention in the manufacture of a medicament for the treatment or prevention of disease.

As will be apparent, preferred features and characteristics of one aspect of the invention are applicable to many other aspects of the invention.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

The invention is hereinafter described by way of the following non-limiting Examples and with reference to the accompanying figures.

DETAILED DESCRIPTION

General Techniques and Definitions

Figure 1:
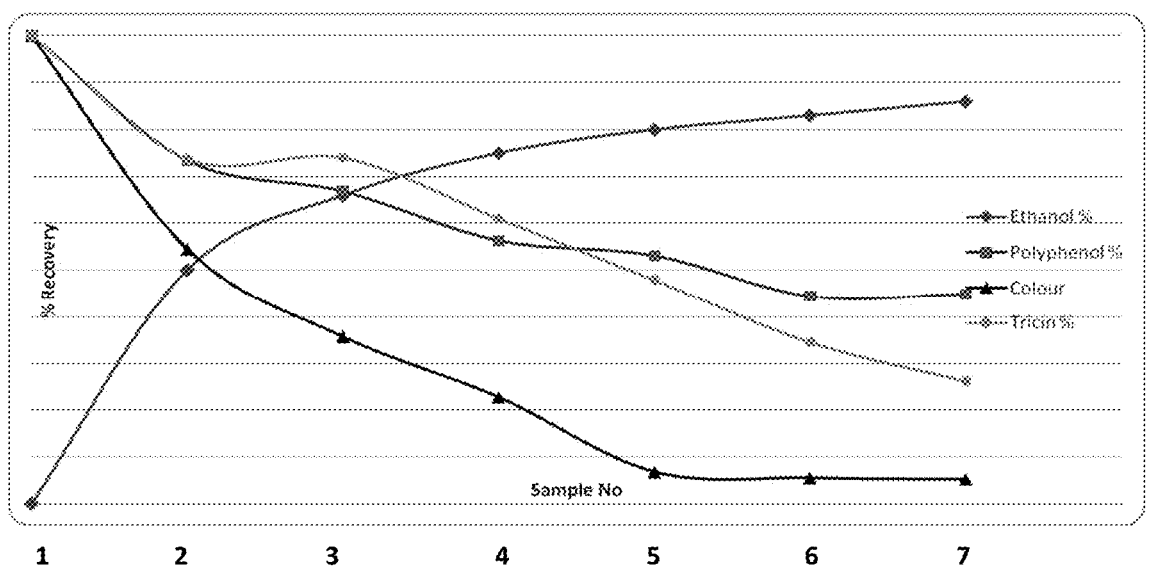
FIG. 1 is an analysis of polyphenols, tricin and colour (A 420 nm) in ethanolic supernatant samples. Sample 1=0% ethanol, sample 2=50% ethanol, sample 3=66% ethanol, sample 4=75% ethanol, sample 5=80% ethanol, sample 6=83% ethanol, sample 7=86% ethanol.
Figure 2:
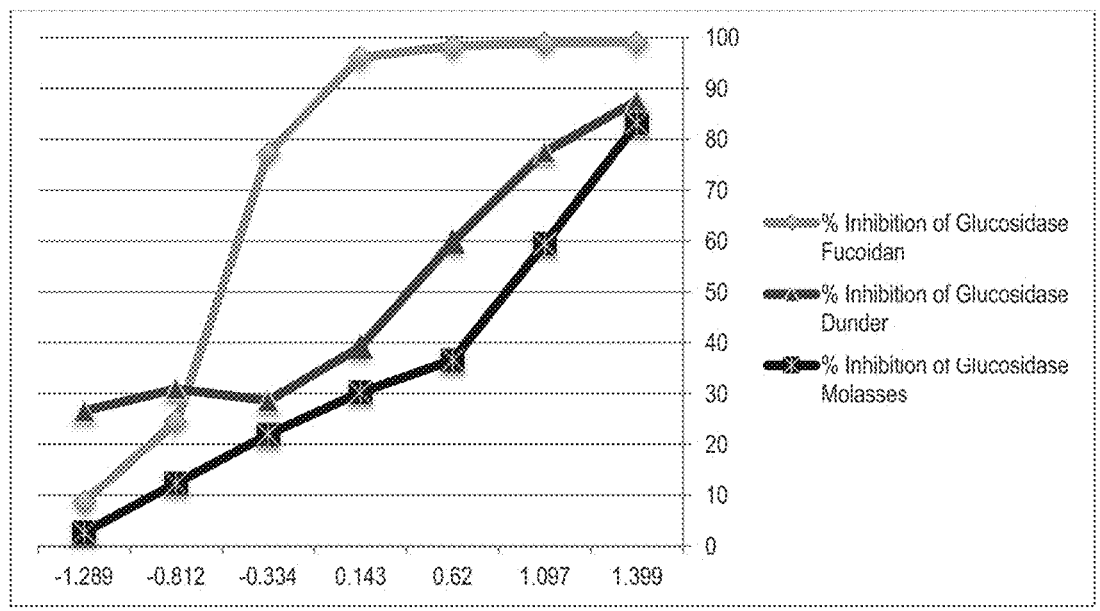
FIG. 2 is a plot of % glucosidase inhibition vs. log 1.4 μg/ml for fucoidan (control), dunder (sample 6) and molasses (sample 3).

Unless specifically defined otherwise, all technical and scientific terms used herein shall be taken to have the same meaning as commonly understood by one of ordinary skill in the art (e.g., chemistry, biochemistry, food and nutritional science, cell culture, molecular biology, and immunology).

Unless otherwise indicated, the recombinant protein, cell culture, and immunological techniques utilized in the present invention are standard procedures, well known to those skilled in the art. Such techniques are described and explained throughout the literature in sources such as, J. Perbal, A Practical Guide to Molecular Cloning, John Wiley and Sons (1984), J. Sambrook et al., Molecular Cloning: A Laboratory Manual, $3^{rd}$ edn, Cold Spring Harbour Laboratory Press (2001), R. Scopes, Protein Purification—Principals and Practice, $3^{rd}$ edn, Springer (1994), T. A. Brown (editor), Essential Molecular Biology: A Practical Approach, Volumes 1 and 2, IRL Press (1991), D. M. Glover and B. D. Hames (editors), DNA Cloning: A Practical Approach, Volumes 1-4, IRL Press (1995 and 1996), and F. M. Ausubel et al. (editors), Current Protocols in Molecular Biology, Greene Pub. Associates and Wiley-Interscience (1988, including all updates until present), Ed Harlow and David Lane (editors) Antibodies: A Laboratory Manual, Cold Spring Harbour Laboratory, (1988), and J. E. Coligan et al. (editors) Current Protocols in Immunology, John Wiley & Sons (including all updates until present).

"Administering" as used herein is to be construed broadly and includes administering an extract or composition comprising the extract as described herein to a subject as well as providing an extract or composition comprising the extract as described herein to a cell.

As used herein, the terms "treating", "treat" or "treatment" include administering a therapeutically effective amount of an extract or composition comprising the extract as described herein sufficient to reduce or delay the onset or progression of a specified disease, or to reduce or eliminate at least one symptom of the disease.

As used herein, the terms "preventing", "prevent" or "prevention" include administering a therapeutically effective amount of an extract or composition comprising the extract sufficient to stop or hinder the development of at least one symptom of the specified condition.

The term "about" as used herein refers to a range of +/−5% of the specified value.

The term "dietary supplement" as used herein is to be construed broadly and means a preparation or formulation which is added to or otherwise included in a subject's normal diet, and is present in addition to the normal diet. A dietary supplement may be administered to a subject prior to, in conjunction with, or after consumption of a food or beverage.

Process for Producing Extract Derived from Sugar Cane

Feedstock for the Extraction Process

After being mechanically harvested, sugar cane is transported to a mill and crushed between serrated rollers. The crushed sugar cane is then pressed to extract the raw sugar juice, while the bagasse (leftover fibrous material) is typically used for fuel. The raw juice is then heated to its boiling point to extract any impurities, then lime and bleaching agents are added and mill mud is removed. The raw juice is further heated under vacuum to concentrate and increase Brix value. The concentrated syrup is seeded to produce bulk sugar crystals and a thick syrup known as molasses. The two are separated by a centrifuge and typically the molasses waste stream is collected for use as a low-grade animal feedstock.

The extract produced according to the process of the invention can be derived from any sugar cane derived product, including those produced during the sugar cane milling process, the sugar cane refining process and other processes using sugar cane products.

Accordingly, the term "sugar cane derived product" as used herein refers to products of the sugar cane milling and refining processes including molasses, bagasse, first expressed juice, mill mud, clarified sugar juice, clarified syrup, treacle, golden syrup, field trash, cane strippings, growing tips, pulp and dunder. These sugar cane derived products comprise complex mixtures of substances including flavonoids, flavones, and polyphenols (Duarte-Almeida et al., 2006; Colombo et al., 2006; Payet et al., 2006; US 2012/0115941) as well as phytosterols, oligosaccharides, polysaccharides, mono and disaccharides, organic acids (e.g. cis and trans aconitic acid), peptides and proteins. The type and amount of these components vary between the different sugar cane derived products. For example, molasses includes mono and disaccharides whereas dunder is almost free of sugar components. This improves the palatability of extracts derived from molasses compared with those derived from dunder, which are bitter and less palatable. This also affects the composition of, for example, polyphenols in extracts derived from molasses compared with dunder. Molasses comprises polyphenols that link to the carbohydrate backbone of mono, di and polysaccharides and cellulose and hemicellulosic materials such as lignans etc. Accordingly, the composition of polyphenols in molasses and dunder differ. Extracts containing compounds such as polyphenols and flavonoids extracted from a sugar cane derived product can be used in the production of, for example, functional foods and beverages and nutritional supplements. Advantageously, extracts that comprise complex mixtures of substances display improved characteristics compared with extracts of isolated components, such as tricin, luteolin or apigenin, or combinations of synthetic compounds. Extracts according to the invention therefore can comprise one or more of tricin, apigenin, luteolin, caffeic acid, hydroxycinnamic acids, sinapic acid, and derivatives thereof. It is believed that natural biological mixtures can have a synergistic effect and may be better than synthetic or individually isolated natural products.

In the process of the invention, the sugar cane derived product is used as a feedstock and mixed with ethanol to form the extraction mixture. Ethanol is used to extract a mixture of flavonoids and/or polyphenols. In contrast, the prior art uses ethanol to crash out impurities either in the extraction of sucrose or during the isolation of individual polyphenols (WO 2004/014159). The skilled person will understand that in order to facilitate extraction of a mixture of flavonoids and/or polyphenols the rate of mixing the feedstock with ethanol may need to be controlled as well as the degree of mixing, ie homogeneity.

The skilled person will understand that in order to facilitate mixing of the sugar cane derived product with ethanol, the sugar cane derived product may need to be mixed with a liquid, typically water, and/or heated in order to achieve a desired viscosity. By way of example, molasses is viscous at room temperature and, as a consequence, mixing of molasses and ethanol may be difficult to achieve consistently, efficiently or uniformly unless the viscosity of the molasses is adjusted. In embodiments of the invention in which the sugar cane derived product is molasses, for example, the molasses may be mixed with water at a ratio of molasses to water of from about 75:25 to about 25:75. In one embodiment, the ratio of molasses to water is about 50:50.

The sugar cane derived product, either mixed with water or not, may be heated to decrease viscosity. For example, sugar cane derived product may be heated to about 25° C. to about 60° C., more preferably about 25° C. to about 40° C., more preferably about 26° C. to about 30° C.

For sugar cane derived products comprising solid material such as bagasse, field trash and cane strippings, it is desirable that the product is first blended or homogenised with water prior to mixing with ethanol to form the extraction mixture. The amount of water with which the sugar cane derived product is blended or homogenised can be readily determined by the skilled person in order to achieve a sugar cane derived product having a suitable viscosity for mixing with ethanol to form an extraction mixture.

Preferably the sugar cane derived product will have a viscosity less than or equal to about 100 centipoise, more preferably between about 50 to about 100 centipoise.

The high viscosity of molasses is as a result of the high total solids (particularly soluble carbohydrates) and this is typically measured by determination of Brix degrees. Preferably the sugar cane derived product will have about 20° to about 50° Brix. Feedstocks with high Brix (>50°) behave differently to lower Brix feedstocks (<30°) with respect to the separation of polyphenols and colour by increasing levels of ethanol. This observation is crucial in both small and large scale separation processes.

In the process of the invention, it is also desirable that extremes of pH be avoided in the extraction mixture. Extreme pH can have a deleterious effect on the components of the extraction mixture. Accordingly, in one embodiment the extraction mixture has a pH of about pH 4 to about pH 7.5.

The extract derived from the process of the invention may be used without further purification. Optionally, the extract may be subjected to purification, preferably hydrophobic interaction chromatography. The purification step removes impurities, such as pigments that contribute to the colour of the extract. In contrast, the prior art uses chromatography to isolate fractions of individual polyphenols (WO 2004/014159).

Addition of Ethanol to the Sugar Cane Derived Product

To extract compounds such as polyphenols and flavonoids, the sugar cane derived product is mixed with ethanol to form an extraction mixture. The present inventors have found that producing an extraction mixture comprising at least 50% v/v ethanol results in an increase in precipitate formation in the reaction mixture. Upon removal of the precipitate, the retained supernatant advantageously has reduced colour and bitterness compared to a supernatant prepared from an extraction mixture comprising less than 50% v/v ethanol.

In addition, the present inventors found that increasing the concentration of ethanol in the extraction mixture above 50% v/v resulted in further reduction in the colour of the retained supernatant once the precipitate had been removed (FIG. 1). Accordingly, in one embodiment, the extraction mixture comprises at least 50% v/v ethanol. In another embodiment, the extraction mixture comprises at least 51%, 52%, 53%, 54%, 55%, 56%, 57%, 58%, 59%, 60%, 65%, 70%, or 75% v/v ethanol, or at least 80%, 81%, 82%, 83%, 84% or 85 ethanol v/v.

The present inventors have found that the optimal concentration of ethanol in the extraction mixture for removing colour in the supernatant while minimising reduction in polyphenols is about 75% to about 85% v/v. Accordingly, in one embodiment, the extraction mixture comprises about 75% to about 85% v/v ethanol. In another embodiment, the extraction mixture comprises about 83% v/v ethanol.

The present inventors also found that while colour removal was substantially achieved with a reaction mixture comprising about 70% v/v ethanol, an extraction mixture comprising about 80% to about 83% v/v ethanol produced an extract that was stable and produced no precipitate over a 6 month period. Thus, in one embodiment of the process according to the invention, the extraction mixture comprises about 80% to about 83% v/v ethanol.

Removal of Precipitate and Ethanol

Following the formation of precipitate in the extraction mixture, the precipitate may be removed from the mixture by any suitable method known in the art. For example the precipitate may be removed by centrifugation and the supernatant obtained. Alternatively, the precipitate may be allowed to settle for a time sufficient to allow the supernatant to be obtained while leaving precipitate behind, such as by sedimentation under gravity for example. The skilled person will understand that other techniques such as filtration can be used alone or in combination with centrifugation or sedimentation in order to produce the extract derived from sugar cane.

Once the supernatant has been obtained the ethanol is removed using techniques known in the art. By way of non-limiting example, the ethanol may be removed from the supernatant by evaporation, such as by using a rotary evaporator with a heating bath at approximately 45° C. or higher. In some instances it may be desirable to further remove water from the supernatant to obtain an aqueous extract having about 64-65° Bx (degrees Brix).

Multiple Extraction Process

In one embodiment of the process of the invention, the process comprises multiple extractions.

In a preliminary extraction, a sugar cane derived product is mixed with ethanol to produce a preliminary extraction mixture (e.g., comprising at least about 25% v/v ethanol), a precipitate is allowed to form in the preliminary extraction mixture and the precipitate is removed from the preliminary extraction mixture to obtain a preliminary supernatant.

Then, in a further extraction, the preliminary supernatant is mixed with ethanol to produce a further extraction mixture comprising at least about 50% v/v ethanol, a precipitate is allowed to form in the further extraction mixture, the precipitate is removed from the further extraction mixture to obtain a further supernatant and ethanol is removed from the further supernatant to produce an extract derived from sugar cane. Further ethanol can be added to a 50% extract supernatant to an ethanol level between 75-83% ethanol. A further precipitate forms and can be recovered. The supernatant can become the final extract.

Fractionation of the Extract

In one embodiment of the process of the invention, the supernatant comprising ethanol, or the extract from which ethanol has been removed, is fractionated to produce the extract derived from sugar cane. By way of non-limiting example, the supernatant or extract may be subject to membrane filtration, size exclusion chromatography, ion exchange chromatography, and or hydrophobic interaction chromatography.

There are several techniques known in the art for separating compounds based on size. For example, it is known in the art that components of a supernatant or extract falling within a specific molecular weight range may be separated by size exclusion processing methods such as gel permeation chromatography or ultrafiltration.

Separation of components in the supernatant or extract may also be achieved using chromatographic techniques or combinations of techniques such as ion exchange chromatography, hydrophobic interaction chromatography, such as for example on XAD or preferably a food grade resin such as FPX66 resin, which may use fractional elution by stepwise increase in pH or with suitable solvents, liquid chromatography-mass spectrometry (LCMS) and/or matrix-assisted laser desorption/ionization-time of flight (MALDI-TOF) to produce the extract.

The supernatants or extracts may be further processed by standard techniques such as but not limited to microfiltration, reverse osmosis, gel permeation, vacuum evaporation and freeze drying, spray drying and tunnel drying.

Testing Extracts for Biological Activity

Sugar cane derived extracts according to the invention may be tested for biological activity using known techniques and assays. For example, an extract according to the invention can be tested for enzymatic activity. By way of non-limiting examples, the extracts may be tested for α-glucosidase inhibitory activity and/or α-amylase inhibitory activity.

As known in the art, α-glucosidase inhibitory activity can be measured as the ability of test samples to prevent the hydrolysis of 4-methylumbelliferyl-α-D-glucopyranosidase by yeast (*Saccharomyces cerevisiae*) α-glucosidase using known techniques. As will be understood by the skilled person, acarbose can be included in the assay as a positive control.

In addition, α-amylase inhibitory activity may be measured by the ability of samples to slow the rate at which porcine pancreatic amylase hydrolyses labelled starch (E-11954, Molecular Probes). As understood in the art, acarbose may be included in the assay as a positive control.

An extract according to the invention can also be tested for anti-inflammatory activity. By way of a non-limiting example, the extracts may be tested for prostaglandin E2 (PGE2) activity. As known in the art, PGE2 inhibitory activity can be measured by the ability of test samples to inhibit PGE2 production in 3T3 cells when stimulated with calcium ionophore. As understood in the art, aspirin and ibuprofen may be included in the assay as a positive control.

Uses of the Extracts Derived from Sugar Cane

The extracts produced according to the process of the invention can be used in a wide variety of economically useful applications.

Food and Beverages

In one embodiment of the invention, an extract produced by the process of the invention is included in a food or beverage product. Food or beverages according to the invention can be prepared by the skilled person using known techniques. Non-limiting examples of such food or beverage products are baked goods, dairy type foods and drinks, snacks, etc. The amount of the extract to be used in a food or beverage can be variable as the extracts themselves are nutrients.

Thus, the extract may be used in any food or food product such as but not limited to sugar, for example crystallised sugar, confectioneries, snacks (sweet and savoury), cocoa-containing foods, flavours, dairy products including cheeses, butter, ice cream, yoghurt, and other dairy spreads; fat-based products including margarines, spreads, mayonnaise, shortenings, cooking and frying oils, and dressings; cereal-based and bakery products including breads and pastas whether these goods are cooked, baked or otherwise processed; confectioneries including chocolate, candies, chewing gum, desserts, non-dairy toppings, sorbets, icings and other fillings; and other miscellaneous food products including eggs and egg products, processed foods such as soups and pre-prepared pastas.

Thus, the extract may be incorporated into or added to processed foods including but not limited to: breads, pastas, biscuits, sauces, soups, bars, dairy products (for example, milk, yoghurts, cheese, ice cream), cakes, ready-to-eat prepared meals, and breakfast cereals.

In addition, the extracts may be used in beverages, whether hot or cold including coffee, tea, cocoa, cereal, chicory and other plant extract based beverages, alcoholic or non-alcoholic beverages and including colas and other carbonated and non-carbonated soft drinks, fruit juices, juice drinks, dairy-based beverages, and meal replacement drinks.

The extracts may also be added to food grade ingredients such as soluble fiber (e.g. oligofructosaccharide), insoluble fiber (e.g. cocoa bean fiber, sugar cane fiber, oatbran), naturally derived fibers (e.g., hemicelluloses, lignocelluloses), chemically derived fibers (e.g., inulin), flour, starch, modified starch, gelatine, or other food, to produce a unique composition or ingredient with enhanced levels of polyphenols, flavonoids, and/or other phytochemicals derived from sugarcane.

The extract according to the invention is particularly useful for increasing the active phytochemical content of coffee products without increasing bitterness. Roasting coffee beans causes the development of the myriad desired flavours of coffee. The roasting also causes the bitter taste of coffee which is related to an increase in the level of the antioxidants, chlorogenic acid lactones and phenylindanes. The more that coffee beans are roasted, the more chlorogenic lactones and phenylindanes are produced. The extract of the invention can be used to increase the level of active phytochemicals (such as polyphenols) in coffee products.

The food or beverage of the present invention can include additional ingredients including an orally ingestible diluent or carrier. Many orally ingestible diluents or carriers are known in the food sciences. These include, but are not limited to, manufactured cereals, fruit or vegetable products, beverages or beverage concentrates, ground meat products or vegetable analogues thereof, and any inert diluent, carrier, or excipient known in the pharmaceutical art.

Nutritional Supplements and Sports Nutrition Products

The extract produced according to the process of the invention may be added to or included in a nutritional supplement. As used herein, a "nutritional supplement" is an orally ingestible product consumed to improve overall nutrition, health, well-being, or performance of a subject in an activity and/or an orally ingestible product which provides additional perceived nutritional or biological benefit to a subject. As would be understood, the nutritional supplement may be provided in a concentrated form, thus allowing for the addition of the nutritional supplement to a food or drink product to allow for the consumption of a desired quantity of an extract of the invention in a reasonable serving size.

In one embodiment the nutritional supplement is a sports nutrition product. Thus, the extract may be added to a sports nutrition product including, by way of non-limiting examples, sports powders, sports drinks, energy drinks, pre-mixes, juices, energy bars, energy gels, isotonic drinks and gelatine, starch based or pectin jellies.

The nutritional supplements and sports nutrition products of the current invention can include additional ingredients. In some embodiments, more than one of the extracts of the current invention can be included in the same nutritional supplement or sports nutrition formulation. Other additional ingredients include any ingestible product. Preferred additional ingredients include, but are not limited to, other active food supplement ingredients such as micro-nutrients such as vitamins and minerals or macro-nutrients such as polyunsaturated fatty acids or fiber. The food additive may also include acceptable dispersing and suspending agents, and water. Other conventional nutritional supplements can also be included if desired. The nutritional supplement or sports nutrition product can take many forms including, but not limited to, powders, liquids, tablets, capsules, solutions, concentrates, syrups, suspensions, or dispersions.

Low GI Products

The glycaemic index or GI ranks carbohydrates according to their effect on blood glucose levels. The lower the GI, the slower the rise in blood glucose level will be when the food is consumed. Some research has shown that by eating a diet with a lower GI, people with diabetes, for example, can reduce their average blood glucose levels. This is important in reducing the risk of developing diabetes-related complications.

To determine a food's GI rating, measured portions of the food containing 10-50 grams of carbohydrate are fed to at least 10 healthy people after an overnight fast. Finger-prick blood samples are taken at 15-30 minute intervals over the next two hours. These blood samples are used to construct a blood sugar response curve for the two hour period. The area under the curve (AUC) is calculated to reflect the total rise in blood glucose levels after eating the test food. The GI rating (%) is calculated by dividing the AUC for the test food by the AUC for the reference food (usually glucose or white bread) and multiplying by 100. A GI value of 55 or less is considered 'low', 56-69 is considered "medium" and over 70 is "high".

A lower glycemic index suggests slower rates of digestion and absorption of carbohydrates and is believed to equate to a lower insulin demand, better long-term blood glucose control and a reduction in blood lipids. It has been shown that individuals who followed a low GI diet over many years were at a significantly lower risk for developing both type 2 diabetes and associated conditions such as cataracts as well as coronary heart disease. High blood glucose levels or repeated glycemic "spikes" following a meal may promote these diseases by both increasing oxidative damage to the vasculature and via the direct increase in insulin levels. Postprandial hyperglycemia has been considered a risk factor mainly associated with diabetes but it is now believed that it also presents an increased risk for atherosclerosis and other conditions in the non-diabetic population.

Low-GI foods, by virtue of their slow digestion and absorption, produce gradual rises in blood sugar and insulin levels and have been shown to improve both glucose and lipid levels in people with diabetes (type 1 and type 2) and have benefits for weight control as they help control appetite and delay hunger. Low GI diets also reduce insulin levels and insulin resistance.

Thus, the extracts produced according to the process of the present invention may be used in food or beverages, for example, to lower or reduce the GI of the food or beverage. By way of example, the extracts according to the present invention in the form of a liquid extract can be sprayed onto standard sugar (whether derived from sugar cane or sugar beets) to produce a low GI sugar. The extracts according to the present invention in the form of a liquid extract can also be sprayed onto other carriers such as flour, starch, bagasse or fiber thus increasing the levels of polyphenols and/or flavonoids in these food ingredients.

Endogenous and "adsorbed" polyphenols and other sugarcane phytochemicals use the fibers to protect these compounds from early metabolic changes in the gut and increase delivery to specific sites in the colon where these compounds reduce inflammation and other disease processes including cyclooxygenase enzymes involved with intestinal carcinogenesis or polyp formation (Cai et al.).

Low Available Calorific Value Products

The available calorific value of a food or beverage relates to the amount of energy available from the food or beverage when digested. The calories in a food or beverage, as well as the GI of the food or beverage, which affects the rate of digestion and absorption, contribute to the available calorific value of the food or beverage. For example, although chocolate is a low-GI food, it contains a high number of calories and therefore has a high available calorific value as determined by conventional methods including bomb calorimetry.

The extracts produced according to the process of the present invention may be used in food or beverages, for example, to lower or reduce the available calorific value of the food or beverage. In addition, or alternatively, the process of the present invention may be used to lower or reduce the available calorific value of a food or beverage by administering the composition of the invention, including the dietary supplement and/or pharmaceutical composition, to a subject prior to, in conjunction with, or after consumption of the food or beverage. In this way when the food or beverage is digested the amount of carbohydrate absorbed is reduced. This effectively reduces the amount of energy available from the food or beverage when digested. By way of example, the extracts according to the present invention in the form of a liquid extract can be sprayed onto standard sugar (whether derived from sugar cane or sugar beets) to produce a reduced available calorific value sugar (sucrose). The extracts according to the present invention in the form of a liquid extract can also be sprayed onto other carriers such as flour, starch or fiber thus increasing the levels of polyphenols and/or flavonoids in these food ingredients. As will be apparent to a skilled person, a powder, such as a freeze dried powder or dehydrated powder, can be used in place of a liquid extract.

Therapeutic and Prophylactic Methods

In the Western diet, 50-70% of dietary calories are derived from carbohydrate. Approximately half are from simple sugars (glucose, fructose, sucrose, lactose, maltose and trehalose) with the remainder coming from complex carbohydrates (hemicelluloses, galactans, mannans and starch).

Complex carbohydrates other than starch are referred to as dietary fiber which is either partly or totally digested in the large intestine.

The digestion of dietary carbohydrates is a physiologically regulated process in the gastrointestinal tract. Important enzymes in this process include salivary and pancreatic α-amylase and intestinal α-glucosidase. Beginning in the mouth, food is chewed and mixed with salivary α-amylase. Starch released begins to break down immediately. This hydrolysis process slows or stops in the stomach because of the change in pH but resumes again in the duodenum where pancreatic α-amylase is secreted. The result is to produce maltose and maltotriose from amylase and maltose, maltotriose, glucose and dextrin from amylopectin.

In the 1960's and 70's, debate began about the possible contributory role of sucrose and fructose in diabetes, obesity and cardiovascular disease. Many research groups suggested that sugar and fructose increased risk of diabetes and heart disease by demonstrating that consuming large amounts elevated blood lipids, glucose, insulin and uric acid. Accordingly the US Senate Select Committee on Nutrition recommended that individuals reduce the amount of sugar in their diets.

Analysis of sugar consumption from 1980 to 2003 in Australia, the United Kingdom and United States of America reveals that per capita consumption of refined sucrose decreased by 23%, 10% and 20% respectively. Prevalence of obesity over the same timeframe has increased 3 fold in Australians. When all sources of nutritive sweeteners, including high fructose corn syrups, were considered, per capita consumption still decreased in Australia (−16%) and the UK (−5%), but increased in the USA (+23%). This suggests that once total energy intake has been accounted for, per capita changes in energy from sucrose may not explain changes in the incidence of obesity. When sucrose, glucose, or starch were replaced with >100 g of fructose/day, a weight gain of 0.44 kg/week was observed in adults. Recent evidence demonstrates that novel sugar cane phytochemicals reduce GI and therefore reduce the risk of obesity and diabetes.

The principal enzymes responsible for the breakdown of carbohydrates in the human body are α-amylase and α-glucosidase and so inhibition of one or both of these enzymes can result in the GI of foods being reduced. The extracts of the invention which demonstrate inhibition of the activity of α-glucosidase and α-amylase in vitro will delay carbohydrate absorption in vivo, thus reducing post-prandial increase in blood glucose. In addition, the extracts of the invention are able to lower the GI of a food or beverage.

Thus, the extracts produced by the process of the invention are of use in the modulation of biological pathways associated with disease including diabetes and metabolic syndrome. Thus, in one aspect, the present invention provides methods of treating or preventing disease by administering to a subject an extract of the invention, a composition of the invention, and/or a food or beverage of the invention.

Compositions and Administration

In certain embodiments, the present invention provides compositions comprising an extract of the invention and a suitable carrier or excipient. In one embodiment, the composition is a pharmaceutical composition comprising a pharmaceutically acceptable carrier. The extracts are incorporated into pharmaceutical compositions suitable for administration to a mammalian subject, e.g., a human. The extracts may be incorporated into the pharmaceutical compositions by way of coating a dosage form. Such compositions typically comprise the "active" compound (i.e. the extract derived from sugar cane) and a "pharmaceutically acceptable carrier". As used hereinafter the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, such media can be used in the compositions of the invention. Supplementary active compounds can also be incorporated into the compositions.

Because the current extract is higher in concentration (polyphenols (mg)/extract (ml)) of polyphenols and lower in colour relative to other extracts from sugar, the extracts are "more effective" in delivering a therapeutic amount of biologically active compounds. The lower colour and organoleptic astringency of some syrups prepared according to the present invention, broaden their possible use and application in a range of foods and carriers.

EXAMPLES

Example 1. Preparation of Extract

Feedstock Preparation 100 ml of Mackay terminal molasses was measured into a glass beaker at room temperature (RT). The weight was 140 g. Then 100 mls of distilled water was added and stirred manually with a glass stirring rod until most of the viscous molasses was mixed with the water. The beaker was then placed on a magnetic stirrer and mixed for 10-15 minutes. The temperature was held at 26-28° C. The pH of this solution was 5.4-5.6.

The final volume was 200 ml. A 1 ml sample was removed and diluted with 1 ml water, mixed well and then a drop was placed on a Ella refractometer. The Brix reading was 48.

Treatment with AR Ethanol (100% v/v)

The feedstock (200 ml) was placed in a glass beaker on a magnetic stirrer and adjusted so that a clear vortex was formed, ethanol was slowly added into the vortex to ensure rapid mixing of the feedstock with the ethanol. Over a period of about 30 minutes, 950 ml of ethanol was added. The temperature was maintained at 26-28° C. This resulted in the final ethanol level in the mixture being 83% v/v. The mixture was stirred for another 30 minutes. A number of sub-samples were taken during the addition of the ethanol to support the observations as the solution changed in colour and different coloured precipitates formed as the ethanol % increased.

Recovery of the 83% Ethanol Supernatant/Extract

The final mixture was turbid and had a coagulated black gelatinous precipitate visibly present in the bottom of the beaker. The supernatant was removed and centrifuged at 4000 rpm (2500×g), for 5 minutes. The clear yellow supernatant was decanted leaving the black precipitate plug in the centrifuge tube. About 950 ml of the mixture was centrifuged and the final volume of supernatant recovered was 880 ml.

Removal of Ethanol from the Supernatant

Ethanol was removed using a Buchi rotary evaporator under vacuum. The bath temperature was 45° C. The final concentrate (free of any ethanol odour) volume was 62 ml and the Brix level was 64-65. Ethanol, its azeotroph and water were all removed during this process.

Bioactive Extract

The final bioactive extract was a dark/yellow colour, free of any particulate material and with a fresh sweet flavour similar to that of golden syrup or treacle.

Example 2. Preparation of Extract

Preparation of Feedstock 200 ml of feedstock was prepared from Mackay terminal molasses as previously described in Example 1. The Brix level was 48.

Addition of AR Ethanol (100%)

1000 ml of ethanol was added in 200 ml increments so the formation, colour and appearance of the precipitate could be observed as the percentage of ethanol increased. Observations were made at 50, 66, 75, 80 and 83% ethanol (v/v), but no samples were collected. The final mixture volume (83% ethanol, v/v) was 1200 ml and this was left standing at 20-25° C. overnight (approximately 18 hours). As before, the ethanol was slowly added into a stirring vortex created by rapid magnetic stirring of the mixture.

Recovery of the 83% Supernatant

The supernatant was recovered in the same way as described in Example 1. The volume was 1050 ml.

Removal of Ethanol

Ethanol was removed at 45° C. under vacuum as described in Example 1. The final syrup volume was 78 ml and the Brix level was 63-65. It had a similar, almost identical dark/yellow colour and taste to the syrup recovered from Example 1.

Observations

At 50% v/v ethanol, an amorphous like floc/precipitate forms and the mixture is a dark to gray colour. Its graininess is similar to the look of curdled milk in coffee.

Further addition of ethanol to 66% v/v results in a significant change as a sticky, gelatinous black mass comes out of solution and starts to settle spontaneously. It appears to be adhering to the glass beaker sides but it also rapidly sediments to the bottom of the beaker. As this black precipitate forms the mixture takes on a clearer yellow but still turbid appearance. The gray amorphous precipitate that formed at 50% seems to have disappeared or it has been "captured" by this new black precipitate. Another possibility is that the 50% precipitate changes (or even redissolves) between 50 and 66% ethanol. These first 2 precipitates up to 66% ethanol are quite significant in terms of the amount of material removed from solution.

As more ethanol is added, further cloudy caramel coloured fine precipitates formed (small amounts) up until the final 83% supernatant was reached. Between 66% to 75% ethanol, a further small sticky black precipitate formed, similar to the one occurring up to 66% ethanol.

Example 3. Preparation of Extract

Preparation of Feedstock 100 ml of molasses from a primary sugar mill was used. The crude molasses had a Brix of 78 using an Atago-Pal 2 digital refractometer. The weight of the material was 145 g. As described in the previous experiments, 100 ml of distilled water was added to the 100 ml of molasses, mixed and stirred for 15 minutes to ensure a homogeneous feedstock. The final feedstock had a Brix of 49-50.

Effect of Adding Increasing Amounts of Ethanol (100% v/v)

Two separate lots of 7 centrifuge tubes were used and 10 ml of feedstock was added to each. To the first 7 tubes, distilled water was added as follows: 0, 10, 20, 30, 40, 50 and 60 ml. To the second 7 tubes, 100% v/v ethanol was added as follows: 0, 10, 20, 30, 40, 50 and 60 ml. All tubes were mixed and shaken 3 times during standing at room temperature (25° C.) for 90 minutes.

Removal of Precipitates

All tubes were centrifuged as described previously. Supernatants were recovered and measured. The appearance of initial mixtures as well as the supernatants and precipitates were recorded by photography (data not shown) and visual descriptions.

Summary of Increasing Ethanol Levels on the Feedstock

The grey precipitate that formed at 50% ethanol was comparably larger than all of the others and quite different in appearance. Increasing ethanol to 66% resulted in a compact black precipitate which was smaller in volume and any signs of the initial grey precipitate which formed initially at 50% ethanol disappeared. At 66% ethanol, the supernatant was clear and dark yellow. As the ethanol level increased, a similar black precipitate resulted, probably slightly more than that formed at 66%. As the percentage ethanol increased, the supernatants became lighter yellow. All supernatants from 66% up were clear (free of any retained turbidity). A summary of these observations is provided in Table 1.

TABLE 1

Summary of observations (ppt = precipitate)

| Tube | Feedstock Vol. mls | Ethanol added mls | % Ethanol | Super Vol. mls | ppt. Vol. mls | Comments |
|---|---|---|---|---|---|---|
| 1 | 10 | 0 | 0 | 9.5 | 0.2-0.3 | Small ppt |
| 2 | 10 | 10 | 50 | 15.5 | 4-5 | Grey ppt large |
| 3 | 10 | 20 | 66 | 27 | 3-3.5 | Black ppt smaller |
| 4 | 10 | 30 | 75 | 29.5 | 4 | Black ppt |
| 5 | 10 | 40 | 80 | 46 | 4 | Black ppt |
| 6 | 10 | 50 | 83 | 55 | 5 | Black ppt |
| 7 | 10 | 60 | 86 | 65 | 6 | Black ppt |

Example 4. Analysis of Extract Polyphenols and Colour

Supernatants were analysed for polyphenols (colorimetric) and colour (A 420 nm) to determine recoveries of polyphenols and degree of removal of colour with increasing levels of ethanol. An analysis of polyphenol levels in supernatants is provided in Table 2, an analysis of tricin in the supernatant samples is provided in Table 3, and an analysis of supernatant sample colour is provided in Table 4.

TABLE 2

Analysis of polyphenols (PP) in supernatant samples.

| Sample | % EtOH | Supernatant (mL) | Solids % | PP (mg/mL) | Total PP (mg) | Recovery % | PP (mg/mL) per unit solids |
|---|---|---|---|---|---|---|---|
| 1 | 0 | 9.5 | 44.8 | 12.71 | 120.70 | 100 | 28.36 |
| 2 | 50 | 15.5 | 33.6 | 5.71 | 88.57 | 73 | 17.01 |
| 3 | 66 | 27 | 13.5 | 2.99 | 80.61 | 67 | 22.12 |
| 4 | 75 | 36 | 8.8 | 1.89 | 67.96 | 56 | 21.45 |
| 5 | 80 | 46 | 6.3 | 1.39 | 64.06 | 53 | 22.11 |
| 6 | 83 | 55 | 4.8 | 0.97 | 53.54 | 44 | 20.28 |
| 7 | 86 | 65 | 4.2 | 0.83 | 54.08 | 45 | 19.81 |

TABLE 3

Analysis of tricin in supernatant samples.

| Sample | % EtOH | Supernatant Vol (mL) | Tricin mg/g | per unit solids | Tricin in supernatant (mg) | % Recovery |
|---|---|---|---|---|---|---|
| 1 | 0 | 9.5 | 0.113 | 0.252 | 1.25 | 100 |
| 2 | 50 | 15.5 | 0.062 | 0.186 | 0.92 | 74 |
| 3 | 66 | 27 | 0.039 | 0.288 | 0.92 | 74 |
| 4 | 75 | 36 | 0.018 | 0.206 | 0.45 | 61 |
| 5 | 80 | 46 | 0.016 | 0.246 | 0.60 | 48 |
| 6 | 83 | 55 | 0.010 | 0.200 | 0.43 | 35 |
| 7 | 86 | 65 | 0.006 | 0.149 | 0.33 | 26 |

TABLE 4

Analysis of supernatant sample colour (colour units at A 420)

| Sample | % EtOH | Supernatant Vol (mL) | Colour units/ml | Total colour | % Recovery |
|---|---|---|---|---|---|
| 1 | 0 | 9.5 | 318.8 | 3028.5 | 100 |
| 2 | 50 | 15.5 | 106.5 | 1650.1 | 54 |
| 3 | 66 | 27 | 40.0 | 1080.0 | 36 |
| 4 | 75 | 36 | 19.2 | 689.8 | 23 |
| 5 | 80 | 46 | 4.5 | 207.6 | 7 |
| 6 | 83 | 55 | 3.1 | 167.9 | 6 |
| 7 | 86 | 65 | 2.5 | 160.6 | 5 |

Example 5. α-Glucosidase Inhibition

α-Glucosidase inhibitory activity is measured as the ability of test samples to prevent the hydrolysis of 4-methyl-umbelliferyl-α-D-glucopyranosidase by yeast (*Saccharomyces cerevisiae*) α-glucosidase.

Table 5 lists the samples tested. Each sample (0.5 mL) was weighed and freeze-dried to determine its % dry matter. The samples were then resuspended in either dimethyl sulfoxide (DMSO) or DMSO:water (1:1) to a concentration of 15 mg/mL, after which the samples were serially diluted.

TABLE 5

Composition of samples tested

| Sample | Sample Description | % Dry matter | Solvent |
|---|---|---|---|
| 1 | Molasses, clarified | 27.50 | DMSO |
| 2 | Molasses, 50-75% ppt in $H_2O$ | 10.91 | DMSO—$H_2O$ |
| 3 | Molasses, 75% supernatant | 43.46 | DMSO |
| 4 | Dunder, clarified | 22.42 | DMSO |

TABLE 5-continued

Composition of samples tested

| Sample | Sample Description | % Dry matter | Solvent |
|---|---|---|---|
| 5 | Dunder, 50-75% ppt in H₂O | 23.92 | DMSO—H₂O |
| 6 | Dunder, 75% supernatant | 32.07 | DMSO |

The substrate, 4-methylumbelliferyl-α-D-glucopyranoside, and enzyme, yeast α-glucosidase, were prepared in the assay buffer, sodium acetate buffer (pH 5.5). The substrate (final concentration 83 µM, 45 µL) was added to 96-well plates containing 45 µL enzyme (final concentration 1.7 mU/mL) and 10 µL of sample. The plate was mixed on an orbital shaker for 30 seconds and incubated for 20 minutes at 37° C. The reaction was stopped by the addition of 100 mM sodium glycine buffer (100 µL, pH 10.6), the plate was shaken for a further 30 seconds, and the fluorescence intensity was measured at $\lambda_{ex}$ 355 nm and $\lambda_{em}$ 460 nm. Fucoidan was used as a positive control and sodium acetate buffer (pH 5.5) was used as a negative control.

All of the samples showed some degree of α-glucosidase inhibitory activity. The highest activity was observed in sample 4 with $IC_{50}$=64 µg/mL and the lowest activity was observed in sample 3 with $IC_{50}$=1,037 µg/mL. All of the samples showed less activity than the positive control fucoidan ($IC_{50}$=0.17 µg/mL). Sample 6 produced a more effective reduction in enzyme activity than sample 3. The skilled person would recognise that, with further concentration, the extracts could contain higher amounts of polyphenols and hence be even more effective in inhibiting α-glucosidase activity.

Example 6. PEG2 Inhibition

The in vitro production of PEG2 from 3T3 cells was measured using the Cayman Chemical Prostaglandin E2 monoclonal EIA (Enzyme Immuno Assay) kit. The cells were exposed to samples 3 and 6 and stimulated with calcium ionophore. The cell supernatants were then assayed for PEG2 production. The cell cytotoxicity of the samples was tested against 3T3 cells to confirm that the observed PEG2 inhibition was not due to cell cytotoxicity. Aspirin and ibuprofen were used as positive controls.

Figure 3:
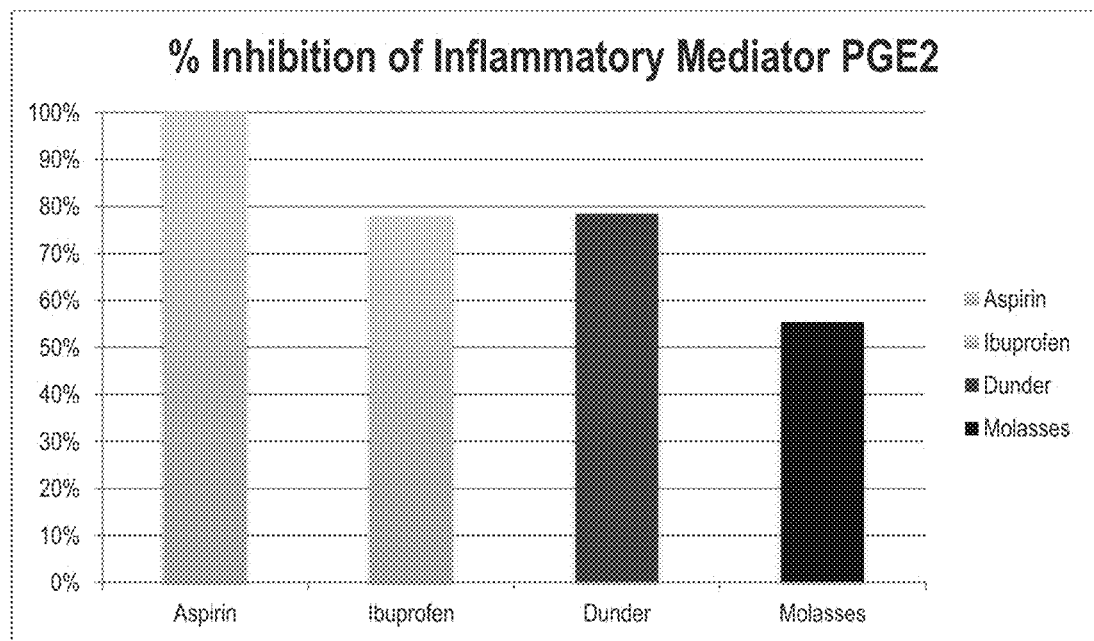
FIG. 3 is a comparison of % PGE2 inhibition for aspirin (control), ibuprofen (control), dunder (sample 6) and molasses (sample 3).

The highest PEG2 inhibition observed for sample 3 and sample 6 was 29.90% and 42.33%, respectively, at 0.488 µg/mL. As shown in FIG. 3, the PEG2 inhibitory response of sample 6 was similar to that of ibuprofen (42.14% at 0.488 µg/mL). Inhibition of PEG2 production in the cells, relative to control cells not exposed to the samples, indicates that the samples act as an anti-inflammatory agent in vitro.

Example 7. Extraction of Polyphenols from Molasses using Ion-Exchange Resins

Ion exchange resins are sometimes used in sugar refineries to remove waste colourants from affination liquor which is produced after the first step towards producing a white sugar. These colourants include melanoidins, caramels (these are Maillard reaction products generated by the reaction between sugars and amino acids driven by temperature and alkaline pH), and natural colourants such as polyphenols and flavonoids. The affination liquor is treated with a resin and sugars and a minor amount of colourants pass through and then this material is further processed to produce food grade molasses (quite different to primary mill molasses). The resin is regenerated with an acid wash and the washings containing some of the colourants and a small amount of polyphenols are discarded. The resin is then washed with an alkaline pH 12-13 solution which removes the bound polyphenols and flavonoids, and this effluent is adjusted to pH 6.5 to 7.0 with acid or preferably it is passed through an acidic resin column to "exchange" the alkali for $H^+$ ions so the effluent pH is less than 7. This process was reproduced in the laboratory on a small scale.

Liquid chromatography profiles of polyphenols were monitored initially in the affination liquor (pH 5.0-6.0) and then in the alkaline resin extracts (pH 12-13) and then after adjusting these extracts (pH 6.5-7.0). Polyphenols are extremely sensitive to high pH conditions forming flavones. Such changes can modify the bioactivity of these compounds and even reversing the pH from alkaline to neutral does not necessarily return them to their previous bioactive properties.

Liquid chromatography fingerprints from alkaline pH 12-13 extracts were significantly different to fingerprints from the same extracts but adjusted to pH 6.5-7.0. A number of major peaks in the alkaline extracts seemed to have shifted to lower elution times on the chromatogram, possibly reflecting the structural change to flavones. When the pH of these alkaline extracts was adjusted to neutral pH, the peaks shifted to longer elution times and aligned themselves with peaks obtained from the original liquor feedstock.

Storing the alkaline extracts for up to 14 days at room temperature did not significantly alter the liquid chromatography fingerprints suggesting that no further changes to flavones was occurring with time. Further, if alkaline extracts were immediately returned back to neutrality, polyphenol peaks also remained stable over 14 days storage.

Example 8. Colour Reduction and Polyphenol Recovery

The present inventors have surprisingly found that colour can be removed efficiently without significant loss of polyphenols. When ethanol concentration was increased beyond 40% a more suitable extract was produced.

Table 6 details the various samples tested.

TABLE 6

Properties of samples tested

| Sample | ICUMSA Colour | Total Phenolics (mg CE/100 g) |
|---|---|---|
| 1 | 32240 | 808 |
| 2 | 37710 | 1356 |
| 3 | 65210 | 1169 |
| 4 | 66030 | 1797 |
| 5 | 32440 | 943 |
| 6 | 10960 | 349 |

Sample 1: Townsville Terminal Molasses, which has been clarified by centrifugation. The crude molasses (about 75 Brix) was adjusted to 25 Brix with water and centrifuged (4,000 rpm for 10 mins). The precipitate was discarded. The initial clarified feedstock was still 25 Brix and used to produce a 75% ethanol supernatant, which is Sample 2. 200 ml of this clarified feedstock was used to make the 75% super extract. Total CE/100 g=808 mg. ICUMSA 32,240.

Sample 2: This 75% super was made by initially removing the 50% precipitate, recovering the 50% super and then adding more ethanol to 75%. Precipitate removed, 75% super recovered and ethanol removed. The final volume was 80 ml and it was 40 Brix. Total CE/100 mg=1356 mg. ICUMSA 37,710.

Sample 3: Dunder with 22 Brix (as all the sugar had been removed). The dunder was centrifuged as above and any precipitate was discarded. 200 ml of this clarified dunder was used to make the 75% super extract (Sample 4). Total CE/100 mg=1169 mg. ICUMSA 65,210.

Sample 4: This 75% super was made by initially removing the 50% precipitate, recovering the 50% super and then adding more ethanol to 75%. Precipitate removed, 75% super recovered and ethanol removed. The final volume was 80 ml and it was 32 Brix.

Sample 5: Hydrophobic chromatography extract of Sample 4. FPX66 material recovered from 15 ml of Sample 4. The peak removed with 70% ethanol was bulked (aliquots were combined) and the ethanol removed. Final volume was 25 ml.

Sample 6: Hydrophobic chromatography extract of Sample 2. FPX66 material recovered from 15 ml of Sample 2. The peak removed with 70% ethanol was bulked (aliquots were combined) and the ethanol removed. Final volume was 40 ml.

The polyphenol recovery and colour reduction calculations are detailed below.

Samples 1 & 2: (i) Polyphenol recovery—200 ml of 25 Brix Molasses=808 mg CE. After dilution, extraction and reduction, 25 Brix increased to 40 Brix (40/25=1.6) and volume reduced from 200 ml to 80 ml (200/80=2.5). Therefore, if 100% recovery of phenols was achieved, total phenolics would have increased to 808 mg CE×2.5=2020 CE. Total phenolics of 1356 CE was detected which means 1356 CE/2020 CE×100=67.13% of total CE was recovered. (ii) Colour reduction—Colour should have theoretically increased 2.5× from 32,240 to 80,600 ICUMSA. Colour detected was however only 37,710 ICUMSA. Colour was therefore reduced by (80,600/37,710) 2.14 times or 42,890 ICUMSA units.

Samples 3 & 4: (i) Polyphenol recovery—200 ml of 22 Brix Dunder=1,169 mg CE. After dilution, extraction and reduction, 22 Brix increased to 32 Brix (32/22=1.45) and volume reduced from 200 ml to 80 ml (200/80=2.5). Therefore, if 100% recovery of phenols was achieved, total phenolics would have increased to 1,169 mg CE×2.5=2,922 CE. Total phenolics of 1,797 CE was detected which means 1,797 CE/2,922 CE×100=61.5% of total CE was recovered. (ii) Colour reduction—Colour should have theoretically increased 2.5× from 65,210 to 163,025 ICUMSA. Colour detected was however only 66,030 ICUMSA. Colour was therefore reduced by (163,025/66,030) 2.5 times or 96,995 ICUMSA units.

Sample 5: (i) Polyphenol recovery—25 ml of Sample 4 made from 15 ml starting volume. Theoretical dilution of phenolics was therefore (15 ml/25 ml=0.6) or 1,797×0.6=1, 078 mg CE. Analysis of Sample 5 was 943 mg CE. This means (943 mg CE/1,078 mg CE) 87.5% of total phenolics were recovered (12.5% were lost). (ii) Colour reduction—Colour should have theoretically decreased 40% from 66,030 to 39,618 ICUMSA. Colour detected was however 32,440 ICUMSA. Colour was therefore reduced by (39, 618−32,440=7,178/39,618=18.1%) or 7,178 ICUMSA units. The FPX66 chromatographic method was therefore more effective at reducing Dunder colour without equivalent loss of phenolics. 12.5/18.1=69.1%. This means that for every ICUMSA colour unit removed only 30.9% of the phenolics were removed.

Sample 6: (i) Polyphenol recovery—40 ml of Sample 2 made from 15 ml starting volume. Theoretical dilution of phenolics was therefore (15 ml/40 ml=0.375) or 1,356× 0.375=508 mg CE. Analysis of Sample 6 was 349 mg CE. This means (349 mg CE/508 mg CE) 68.7% of total phenolics were recovered (31.3% were lost). (ii) Colour reduction—Colour should have theoretically decreased 31.3% from 37,710 to 25,907 ICUMSA. Colour detected was however 10,960 ICUMSA. Colour was therefore reduced by (25,907−10,960=14,947/25,907=57.7%) or 14,947 ICUMSA units. The FPX66 chromatographic method was therefore very effective at reducing molasses colour without equivalent loss of phenolics. 57.7/31.3=54.25% This means that for every ICUMSA colour unit removed only 54.25% of the phenolics were removed.

Figure 4A:
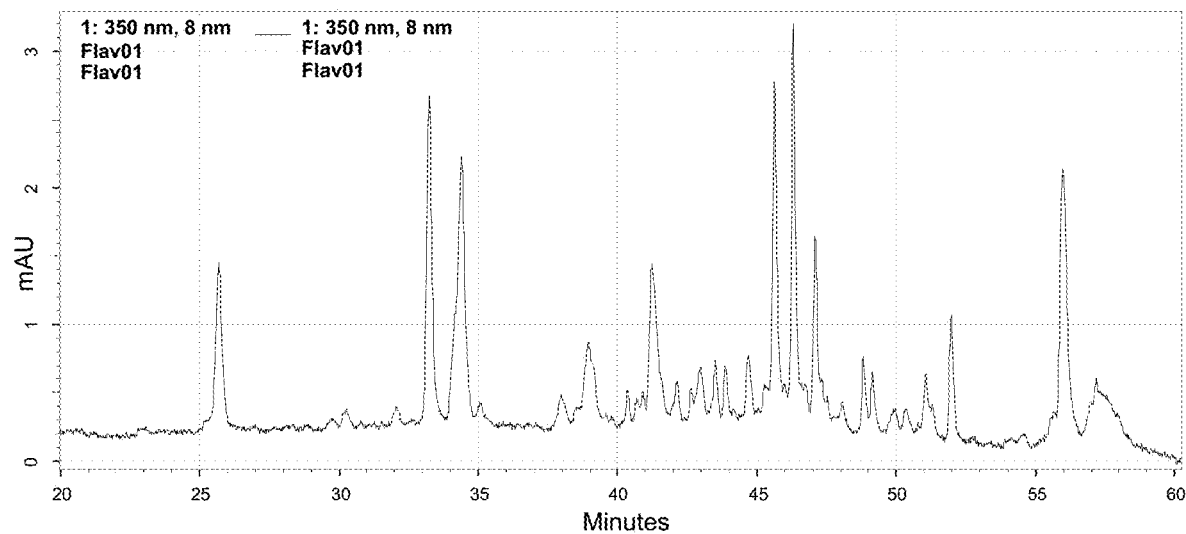
FIG. 4A is an HPLC spectrum of Sample 1.
Figure 4B:
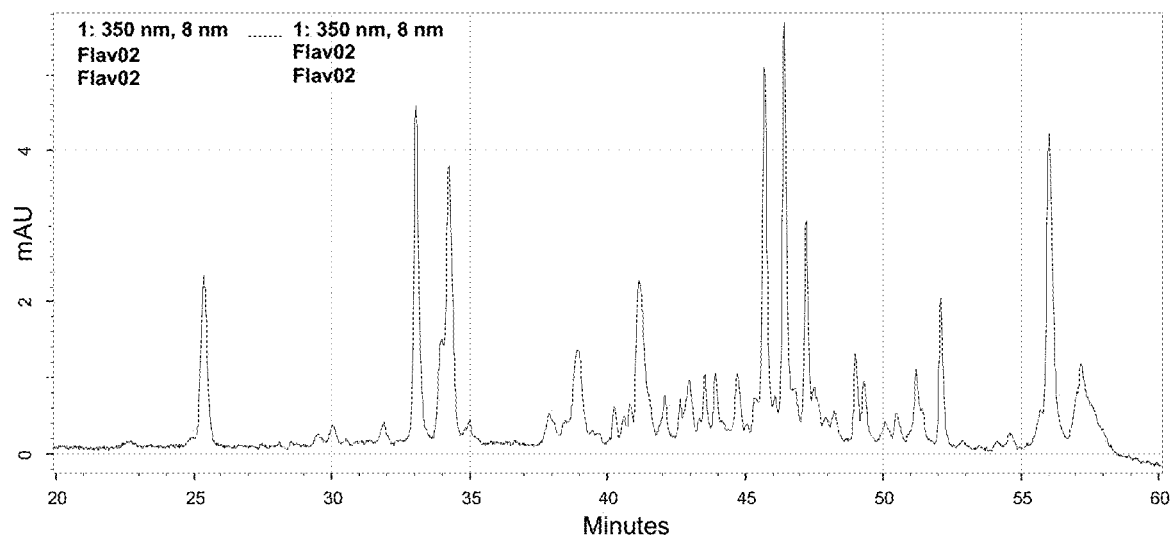
FIG. 4B is an HPLC spectrum of Sample 2.
Figure 4C:
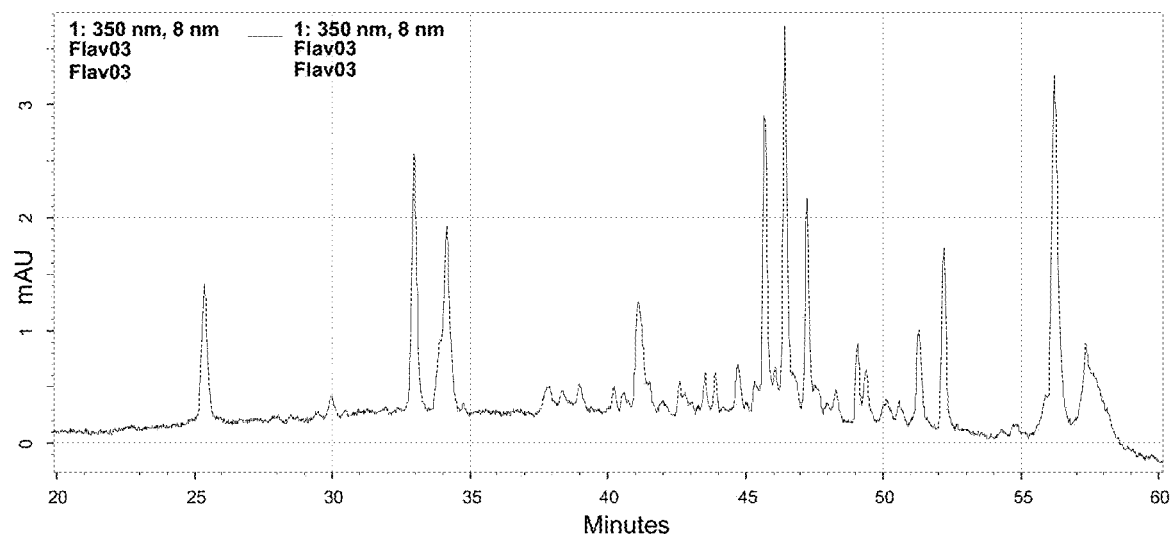
FIG. 4C is an HPLC spectrum of Sample 3.
Figure 4D:
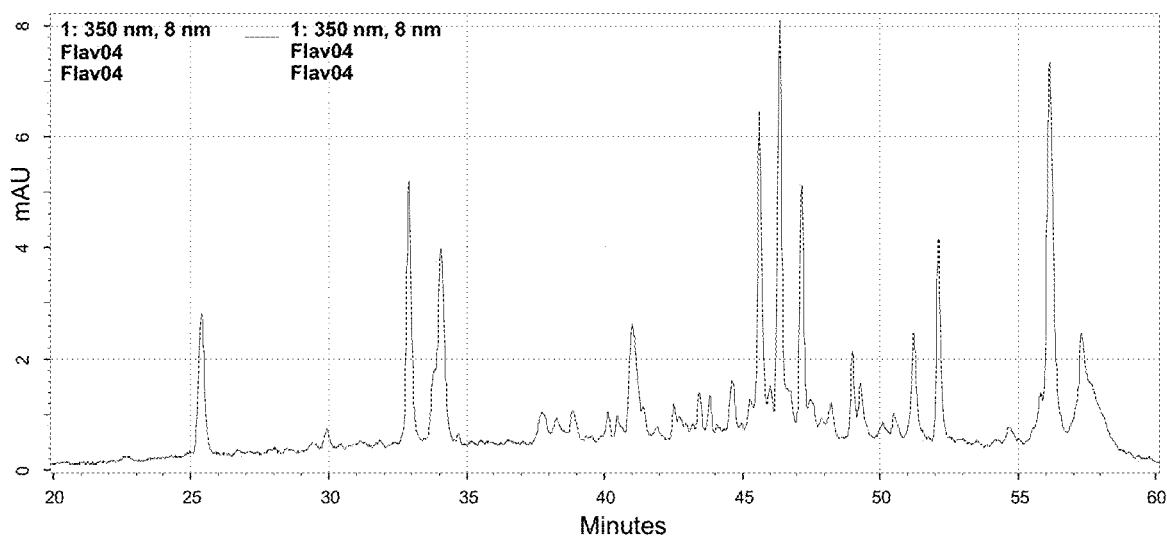
FIG. 4D is an HPLC spectrum of Sample 4.
Figure 4E:
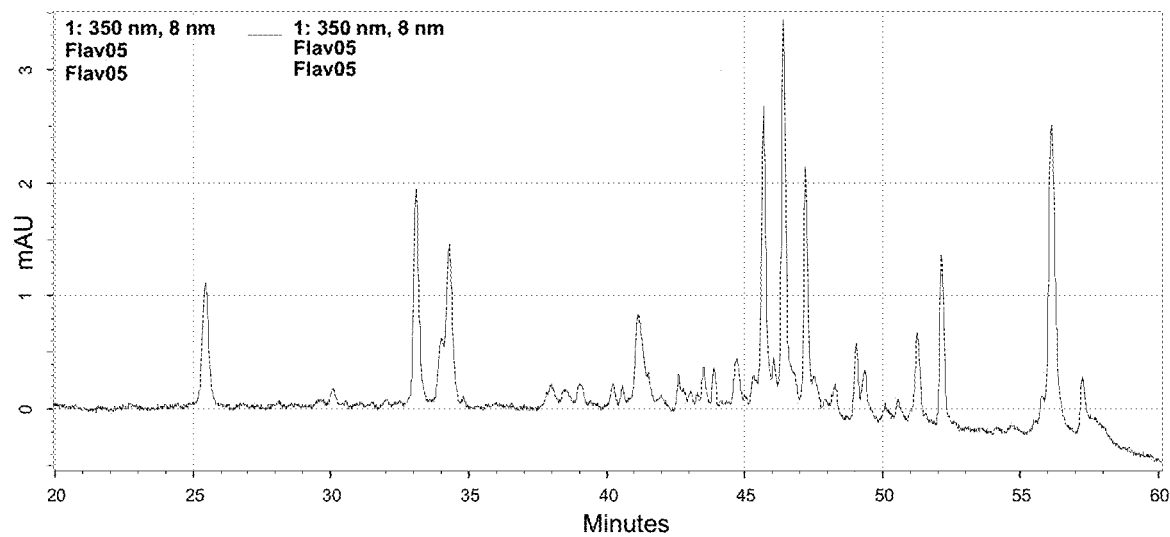
FIG. 4E is an HPLC spectrum of Sample 5.
Figure 4F:
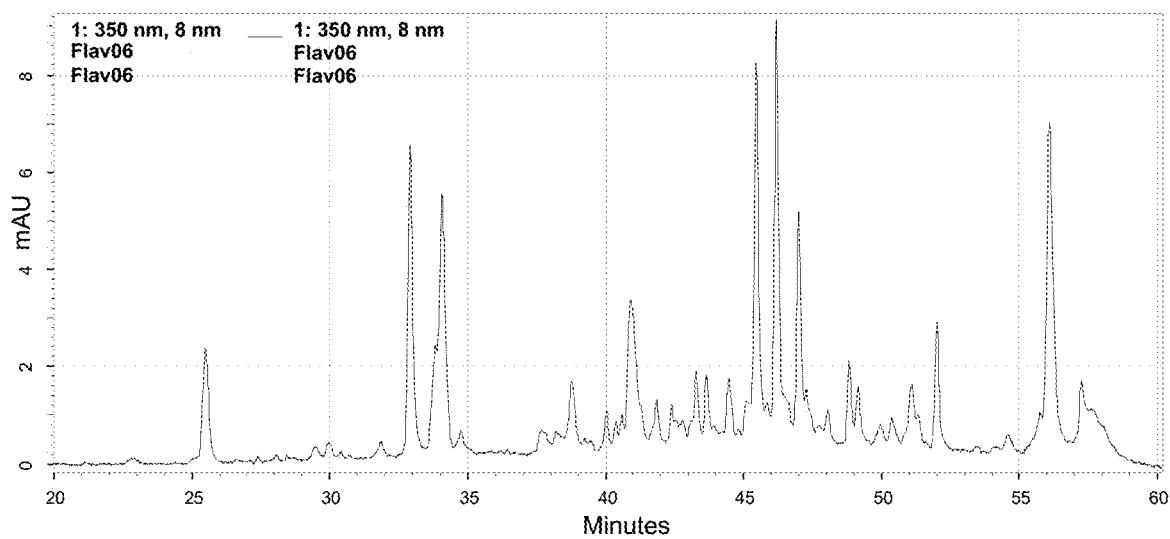
FIG. 4F is an HPLC spectrum of Sample 6.
Figure 4G:
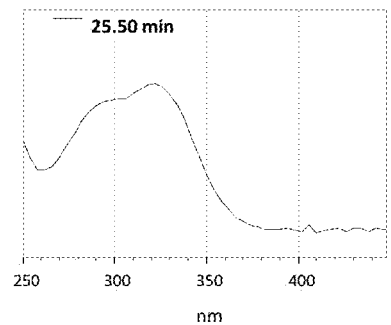
FIG. 4G is an HPLC spectrum of unidentified phenolics at various retention times.
Figure 4G:
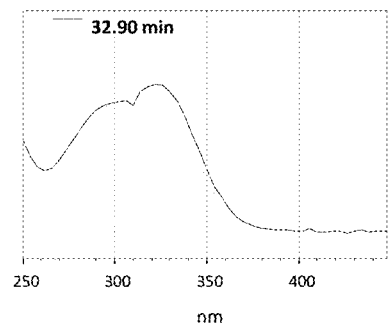
Figure 4G:
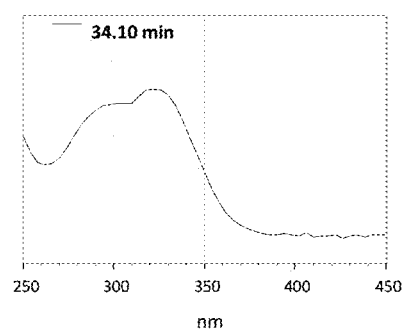
Figure 4G:
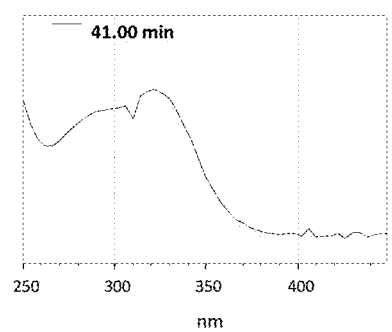
Figure 4H:
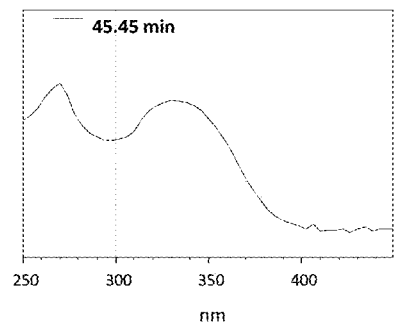
FIG. 4H is an HPLC spectrum of unidentified flavonoids at various retention times.
Figure 4H:
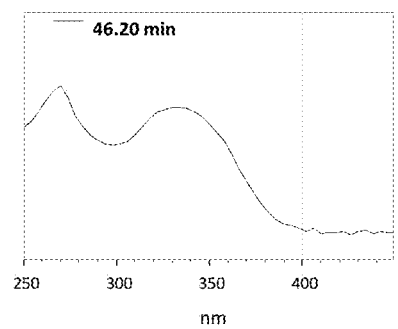
Figure 4H:
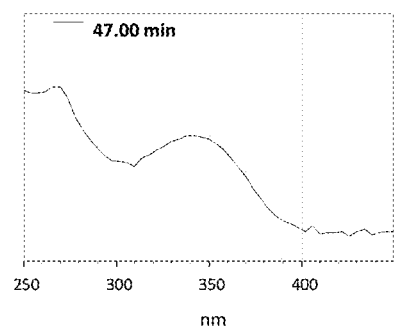
Figure 4H:
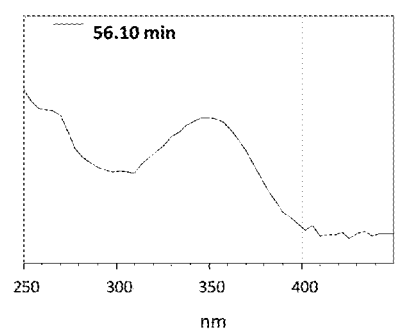

FIG. 4A, FIG. 4B, FIG. 4C, FIG. 4D, FIG. 4E, and FIG. 4F show the HPLC fingerprints of samples 1, 2, 3, 4, 5, and 6, respectively. FIG. 4G and FIG. 4H show spectra of unidentified phenolics and flavonoids at various retention times.

Figure 5:
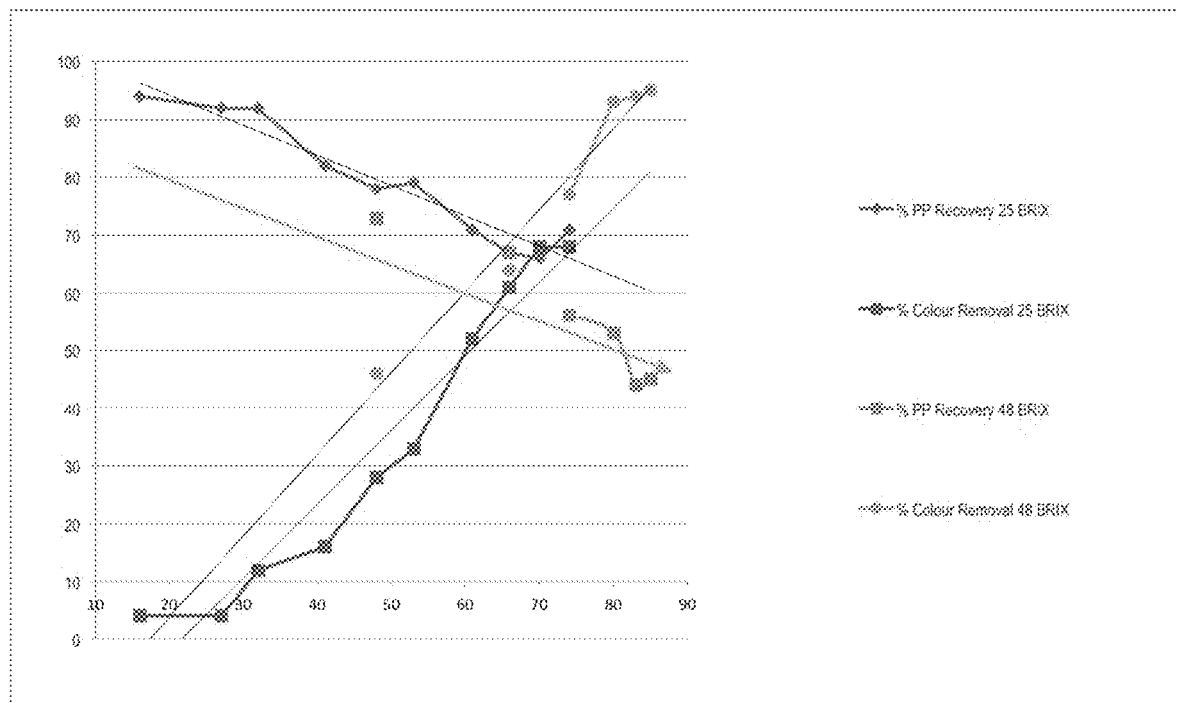
FIG. 5 is a plot of % polyphenol (PP) recovery vs. % ethanol and % colour removal vs. % ethanol of molasses feedstock samples having 25° Brix and 48° Brix. x axis=% ethanol; y axis=% polyphenol recovery and % colour removal.

As shown in FIG. 5, the present inventors observed that 75-85% EtOH is the optimal concentration (which differs from that reported in WO 2004/014159) as it yields maximal colour reduction without significant loss of polyphenols.

Figure 6:
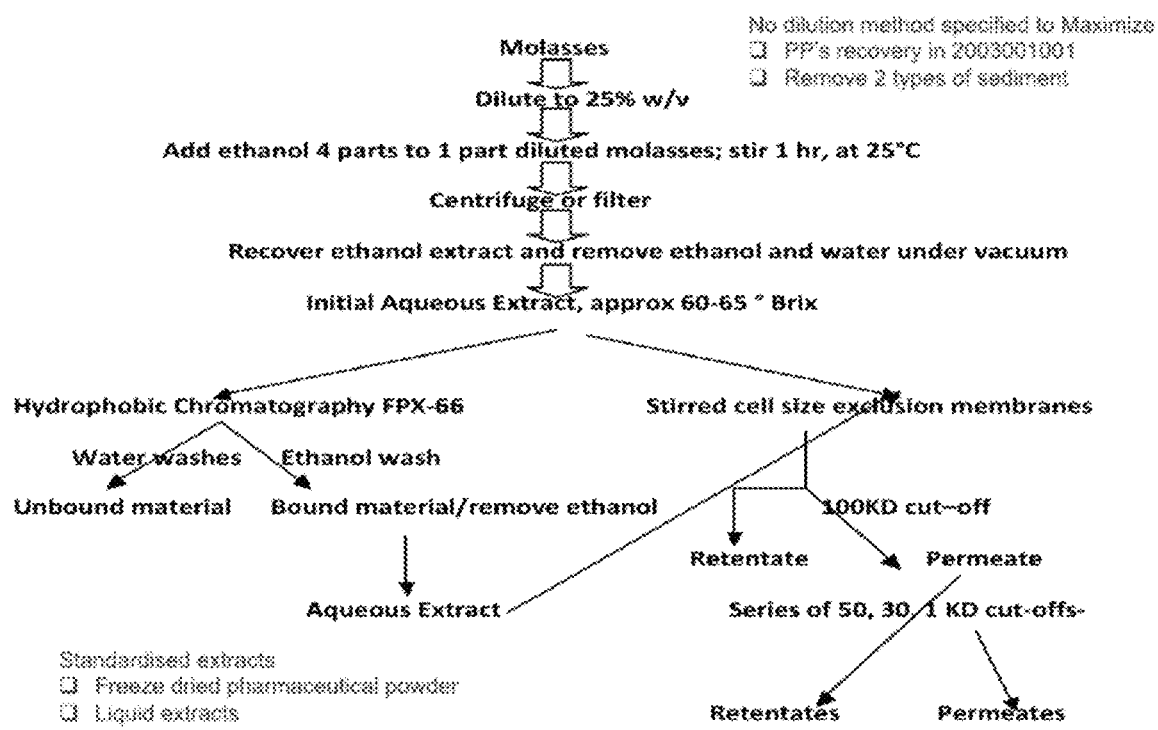
FIG. 6 is a flow chart of an extraction method to produce a standardised extract according to the invention.

The present inventors also observed that, when molasses is diluted to 25 Brix and then 48 Brix and extraction is broken into two stages, the colour of the final extract is lower and polyphenol recovery is higher. Therefore, an extraction method to produce a standardised extract is as set out in FIG. 6.

It will be appreciated by persons skilled in the art that numerous variations and/or modifications may be made to the above-described embodiments, without departing from the broad general scope of the present disclosure. The present embodiments are, therefore, to be considered in all respects as illustrative and not restrictive.

The steps, features, integers, compositions and/or compounds disclosed herein or indicated in the specification of this application individually or collectively, and any and all combinations of two or more of said steps or features.

All publications discussed and/or referenced herein are incorporated herein in their entirety.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed before the priority date of each claim of this application.

REFERENCES

Colombo et al.(2006) Phytochem Anal, 17:337-343.
Duarte-Almeida et al. (2006) Plant Foods for Human Nutrition, 61:187-192.
Cai H et al. (2005) Mol Cancer Ther, 4:1287-1292.
Payet et al. (2006) J Agric Food Chem, 54:7270-7276.

The invention claimed is:

1. A method of treating type II diabetes in a subject, the method comprising administering to the subject an effective amount of a molasses extract derived from molasses having about 20° to about 50° brix and a viscosity of between about 50 to about 100 centipoise,
   wherein the extract is produced by a process comprising:
      i) heating molasses and/or mixing molasses with water in a ratio of 75:25 to 25:75 so as to reduce the viscosity thereof;
      ii) mixing the viscosity reduced molasses with ethanol to produce an extraction mixture comprising from about 70% to about 85% v/v ethanol at a pH of about 4 to about 7.5;
      ii) allowing a precipitate to form in the extraction mixture;
      iii) removing the precipitate from the extraction mixture to obtain a supernatant; and
      iv) removing ethanol from the supernatant to produce the extract, the extract having α-glucosidase inhibitory activity and comprising flavonoids in a concentration of at least 25 mg/mL, polyphenols in a concentration of at least 25 mg/mL and a colour of about 800 to about 140 milliabsorbance units at 420 nm.

2. The method of claim 1, wherein the extract derived from molasses comprises one or more of tricin, apigenin, luteolin, caffeic acid, hydroxycinnamic acids, sinapic acid, and derivatives thereof.

3. A method of treating obesity in a subject, the method comprising administering to the subject an effective amount of a molasses extract derived from molasses having about 20° to about 50° brix and a viscosity of between about 50 to about 100 centipoise,
   wherein the extract is produced by a process comprising:
      i) heating molasses and/or mixing molasses with water in a ratio of 75:25 to 25:75 so as to reduce the viscosity thereof;
      ii) mixing the viscosity reduced molasses with ethanol to produce an extraction mixture comprising from about 70% to about 85% v/v ethanol at a pH of about 4 to about 7.5;
      ii) allowing a precipitate to form in the extraction mixture;
      iii) removing the precipitate from the extraction mixture to obtain a supernatant; and
      iv) removing ethanol from the supernatant to produce the extract, the extract having α-glucosidase inhibitory activity and comprising flavonoids in a concentration of at least 25 mg/ml, polyphenols in a concentration of at least 25 mg/ml and a colour of about 800 to about 140 milliabsorbance units at 420 nm.

4. The method of claim 3, wherein the extract derived from molasses comprises one or more of tricin, apigenin, luteolin, caffeic acid, hydroxycinnamic acids, sinapic acid, and derivatives thereof.

* * * * *